United States Patent
Fuchs et al.

(10) Patent No.: US 6,708,846 B1
(45) Date of Patent: Mar. 23, 2004

(54) DISPENSER FOR FLOWABLE MEDIA

(75) Inventors: Karl-Heinz Fuchs, Radolfzell (DE); Stefan Ritsche, Radolfzell (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/673,009

(22) PCT Filed: Feb. 3, 2000

(86) PCT No.: PCT/EP00/00851
§ 371 (c)(1),
(2), (4) Date: Mar. 8, 2001

(87) PCT Pub. No.: WO00/47332
PCT Pub. Date: Aug. 17, 2000

(30) Foreign Application Priority Data

Feb. 14, 1999 (DE) .......................... 199 05 993
May 21, 1999 (DE) .................... 299 08 923 U

(51) Int. Cl.[7] .............................................. B65D 83/76
(52) U.S. Cl. .................... 222/82; 222/83.5; 222/327; 222/386
(58) Field of Search ...................... 222/82, 83, 83.5, 222/326, 327, 321.6, 386

(56) References Cited

U.S. PATENT DOCUMENTS

| | | | | |
|---|---|---|---|---|
| 4,623,337 A | * | 11/1986 | Maurice | ............... 222/390 |
| 5,469,989 A | | 11/1995 | Graf et al. | |
| 5,813,570 A | * | 9/1998 | Fuchs et al. | ............... 222/82 |
| 5,944,222 A | * | 8/1999 | Fuchs et al. | ............... 222/82 |
| 6,321,942 B1 | * | 11/2001 | Krampen et al. | ............... 222/82 |
| 6,401,987 B1 | * | 6/2002 | Oechsel et al. | ............ 222/321.7 |

FOREIGN PATENT DOCUMENTS

| | | | |
|---|---|---|---|
| DE | 40 21 263 A1 | 1/1992 | |
| DE | 29601047 U1 | * 6/1996 | ........... B65D/55/02 |
| DE | 197 39 989 A1 | 3/1999 | |
| EP | 0 443 519 A2 | 2/1991 | |
| GB | 1193179 A | * 5/1970 | ........... A61M/3/00 |
| GB | 2 041 249 A | 12/1978 | |
| WO | WO 95/24971 | 9/1995 | |
| WO | WO 96/24439 | 8/1996 | |
| WO | WO 00/47332 | 8/2000 | |

* cited by examiner

Primary Examiner—Kenneth Bomberg
(74) Attorney, Agent, or Firm—Quarles & Brady LLP

(57) ABSTRACT

The invention relates to a dispenser, especially a disposable atomizer (25), with a dispenser unit (11). Said unit contains a media container (12) which also forms the pump chamber and which is sealed by a piston-type stopper (14). When activated, said piston-type stopper is punctured by a hollow needle (16). The outlet nozzle (20) surrounds the dispenser unit to a large extent. The dispenser unit (11) can be introduced into an activating unit (26). According to one configuration, this activating unit is pin-shaped with a loading chamber (29). The dispenser unit is held in place by an activating push rod (30) which can be longitudinally displaced when activated by turning (33) and is prestressed by a spring (36). The dispenser is activated by a trigger device (39). The dispenser unit (11) can also be changed after use.

15 Claims, 15 Drawing Sheets

Figure 7:
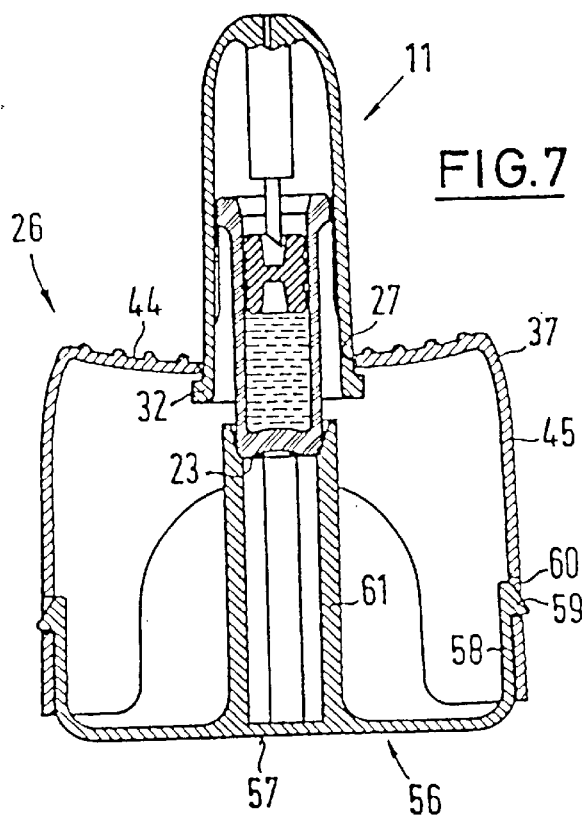

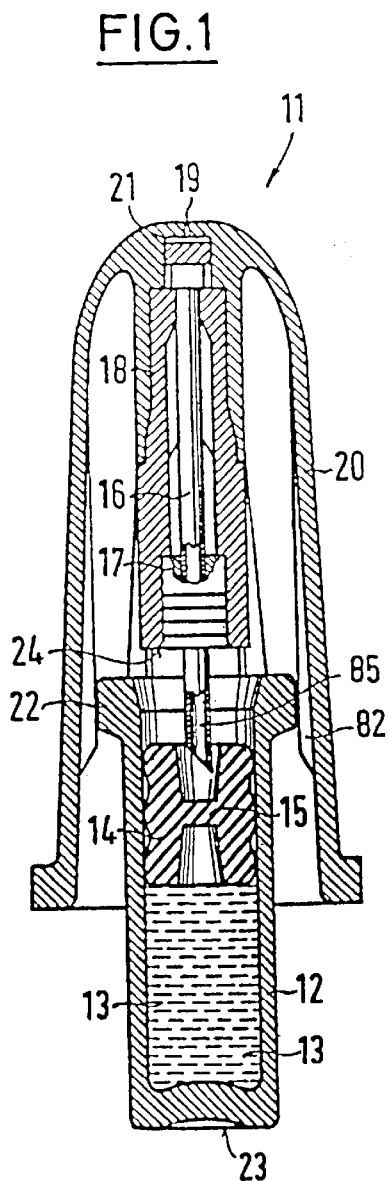
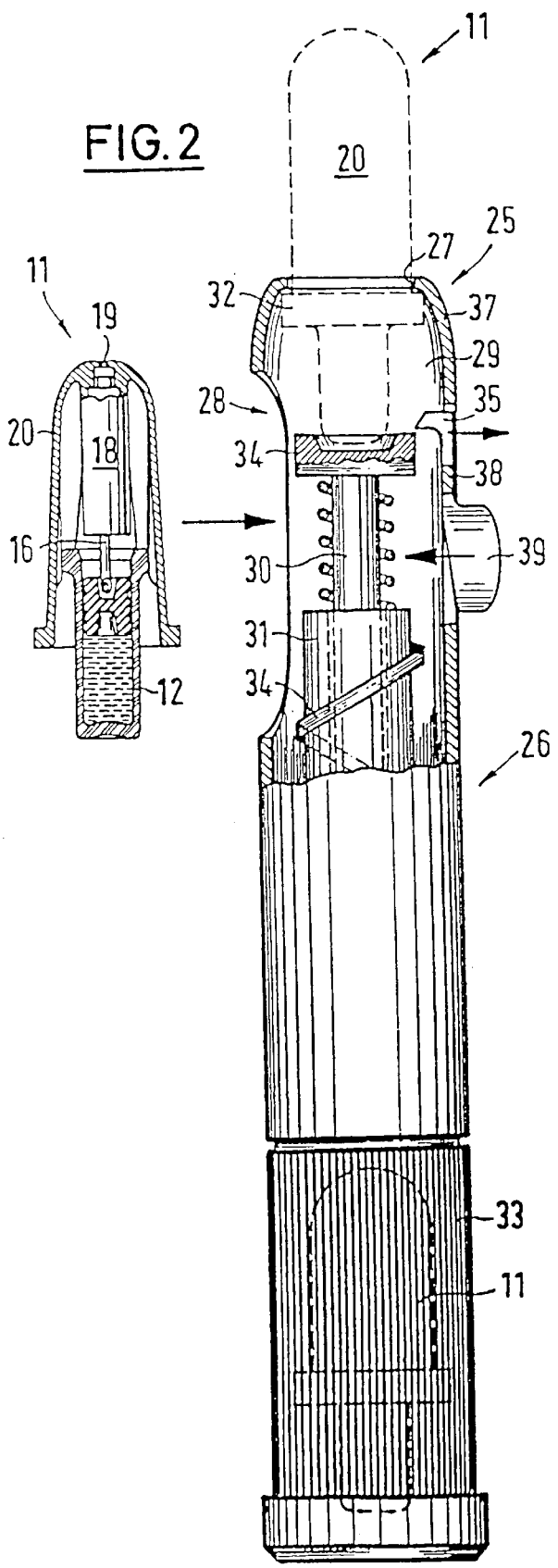

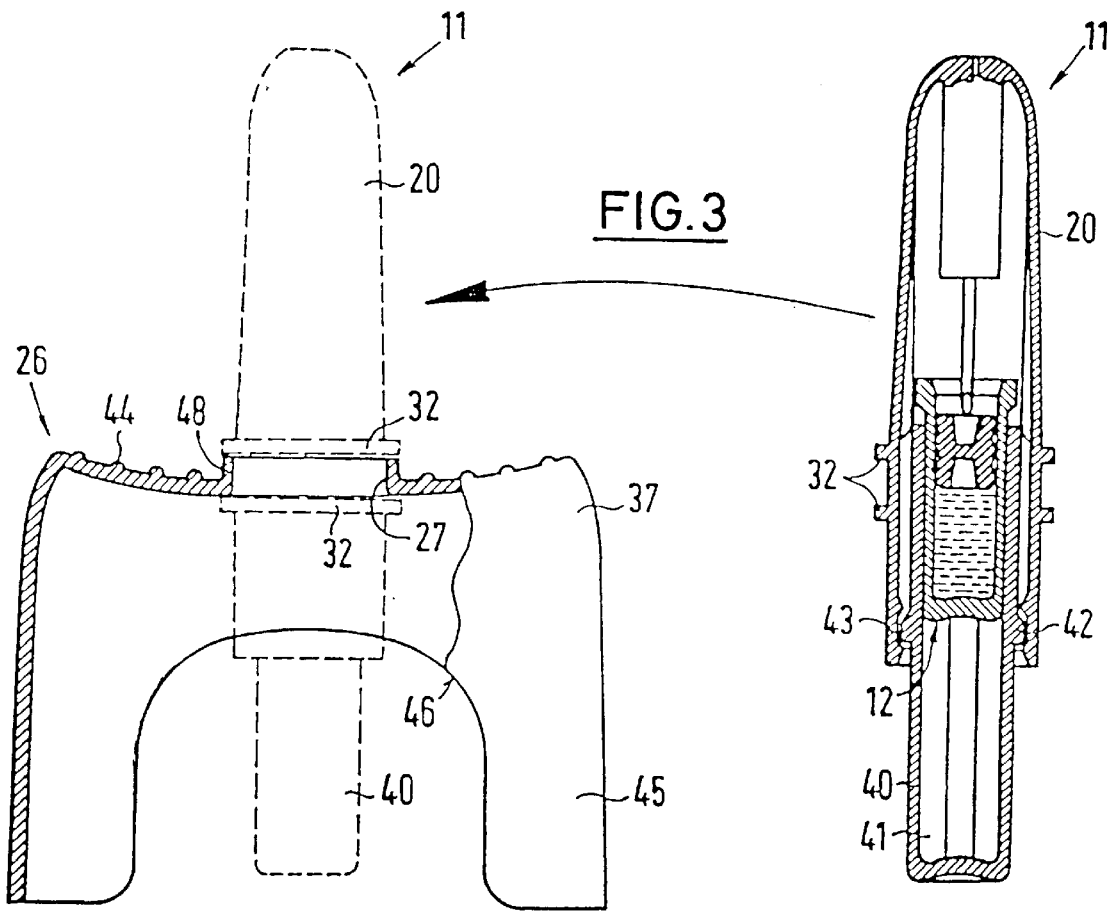
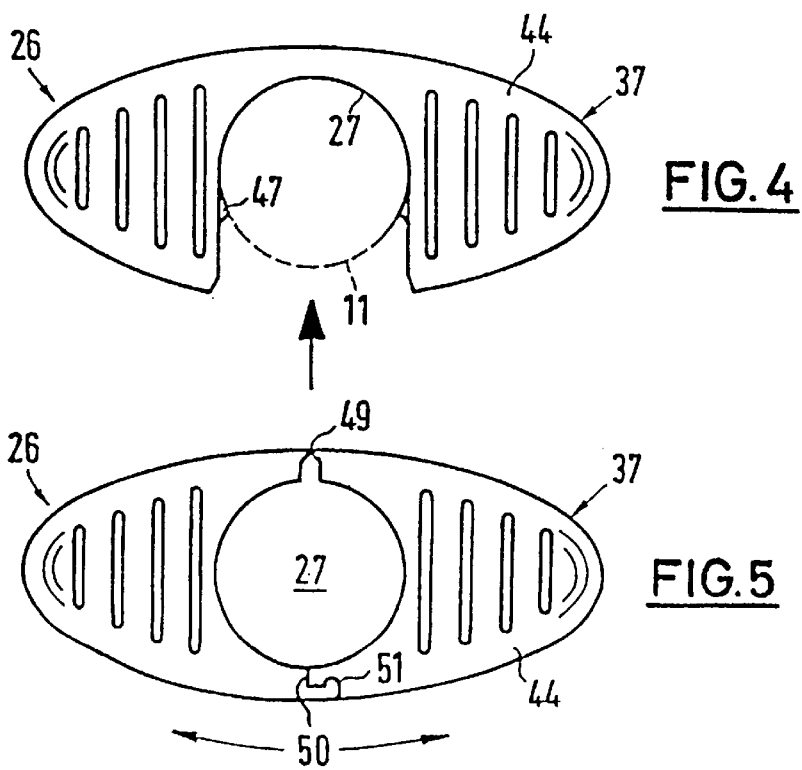

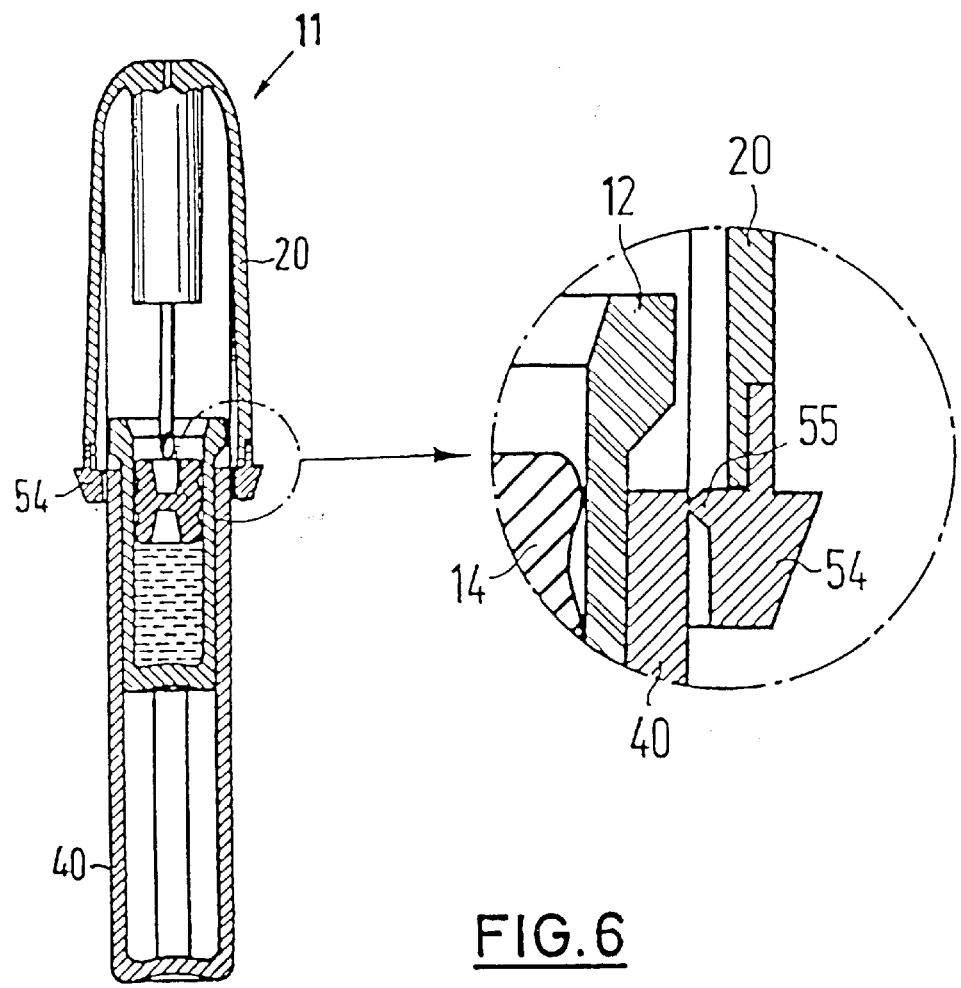
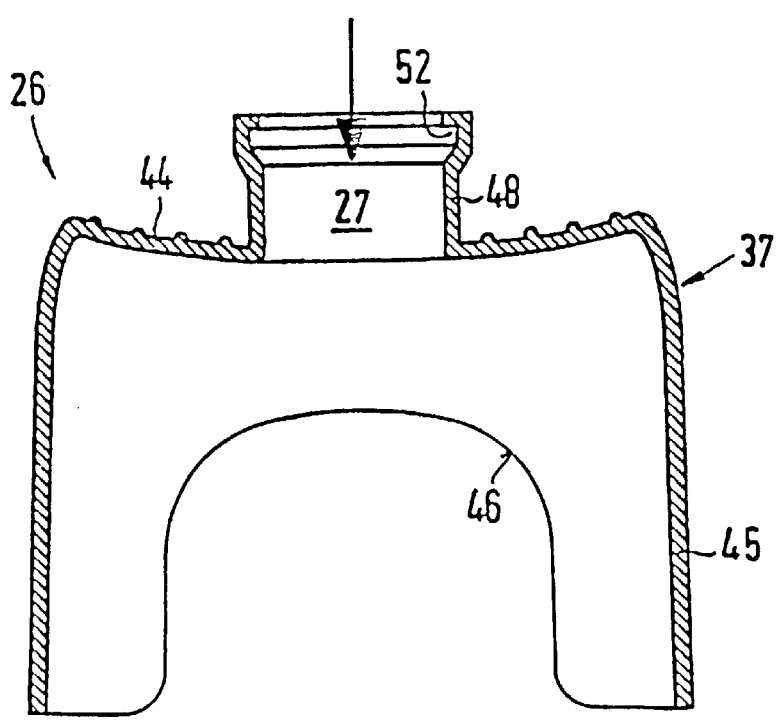
FIG.6

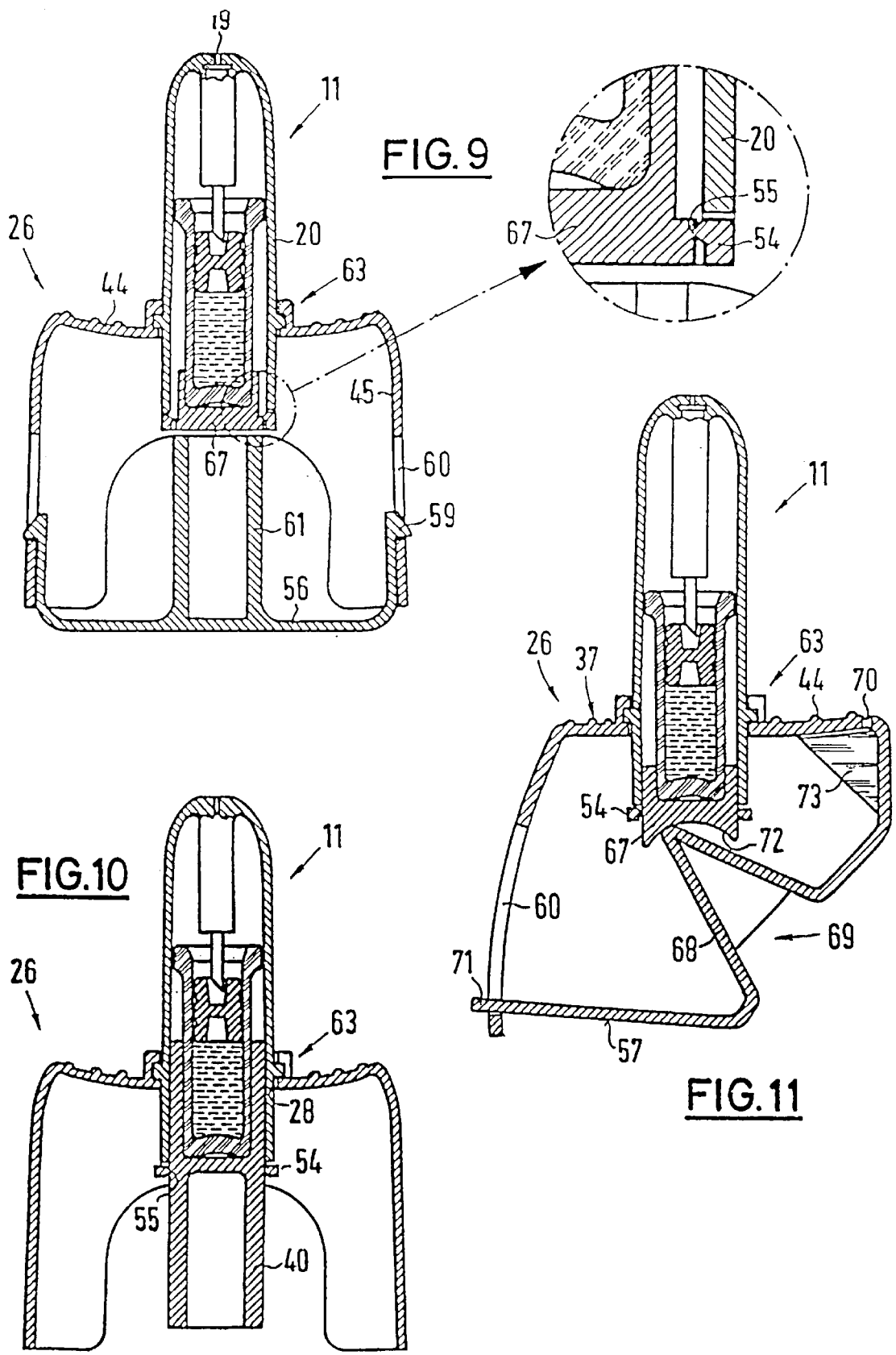

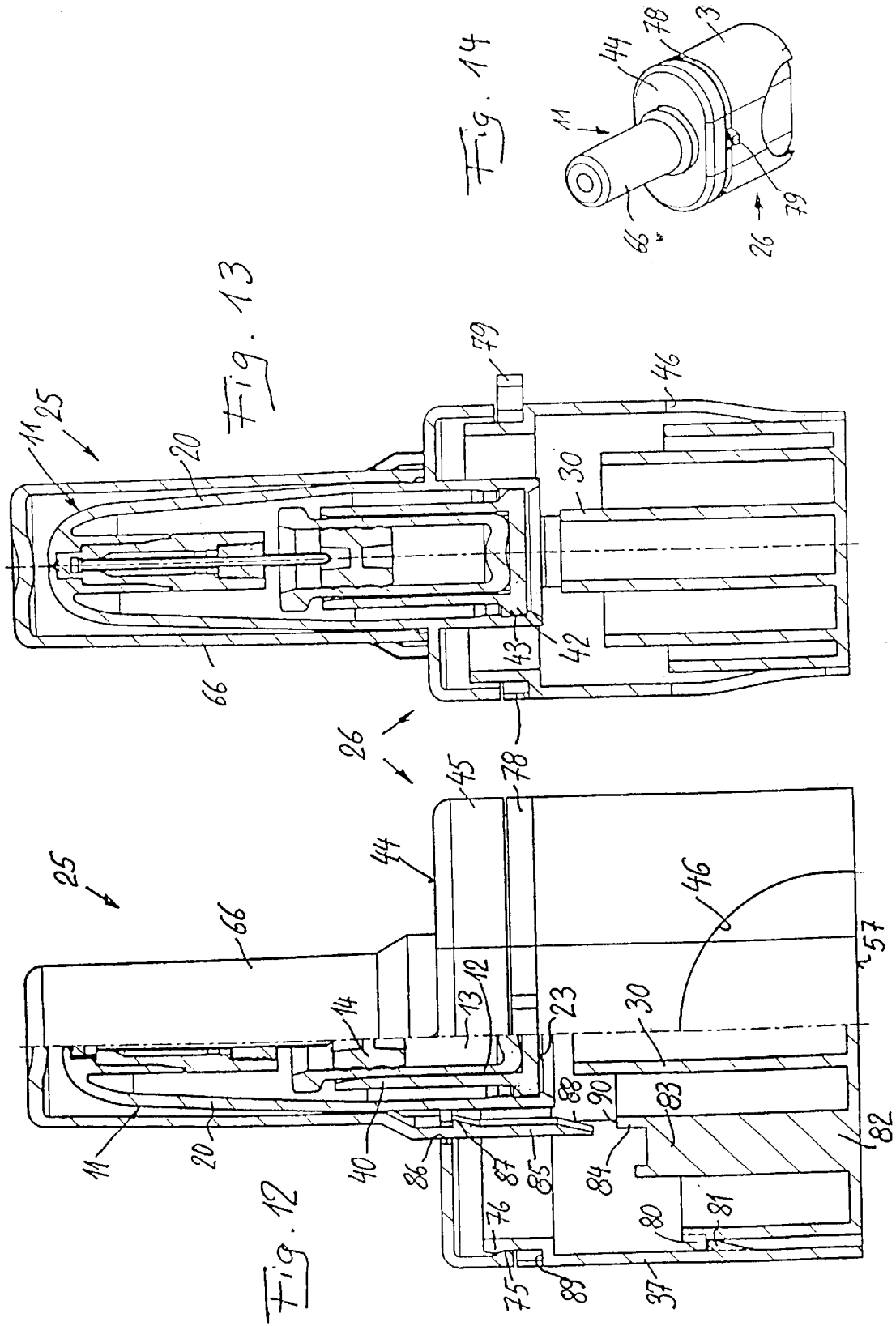

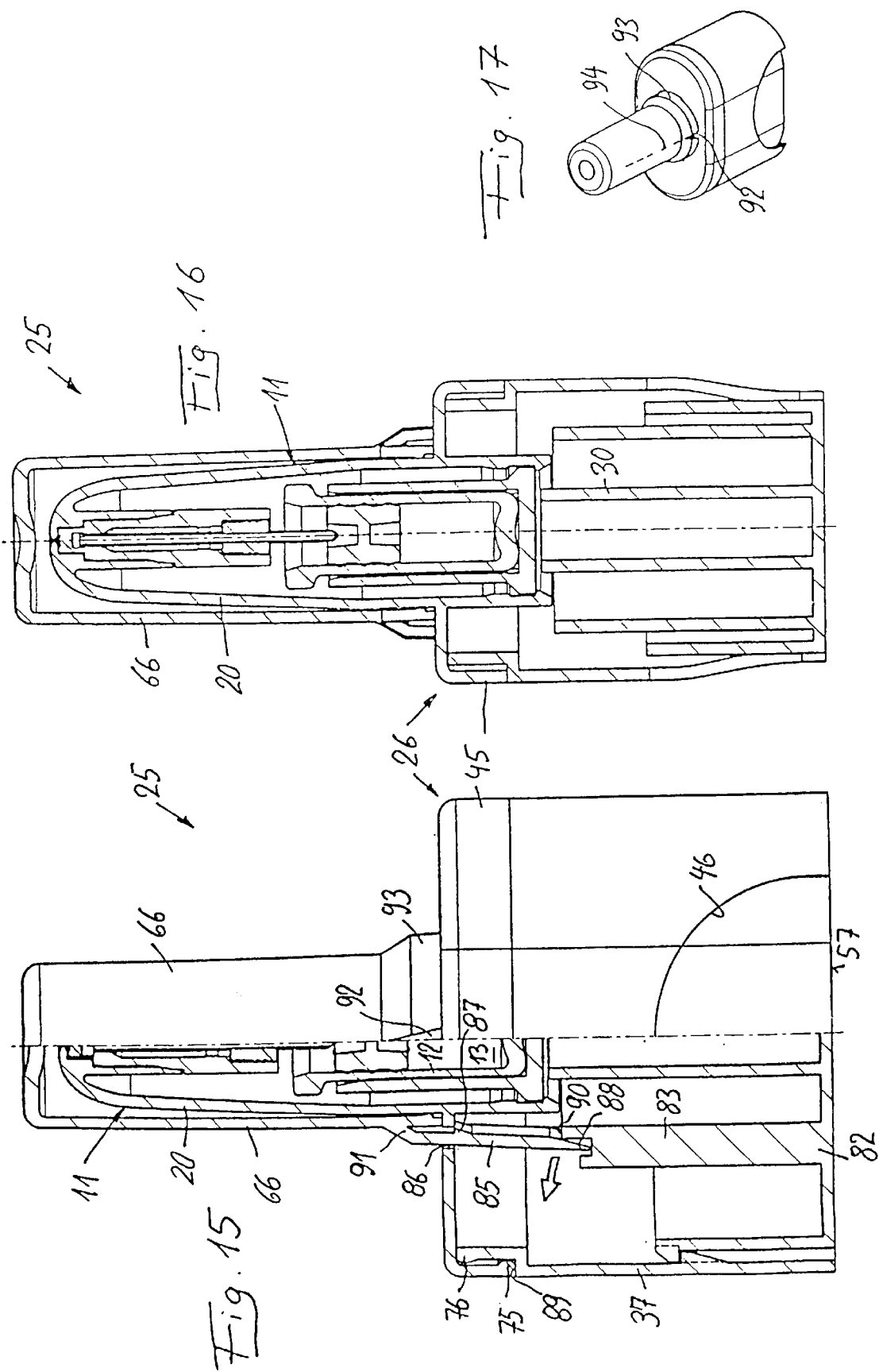

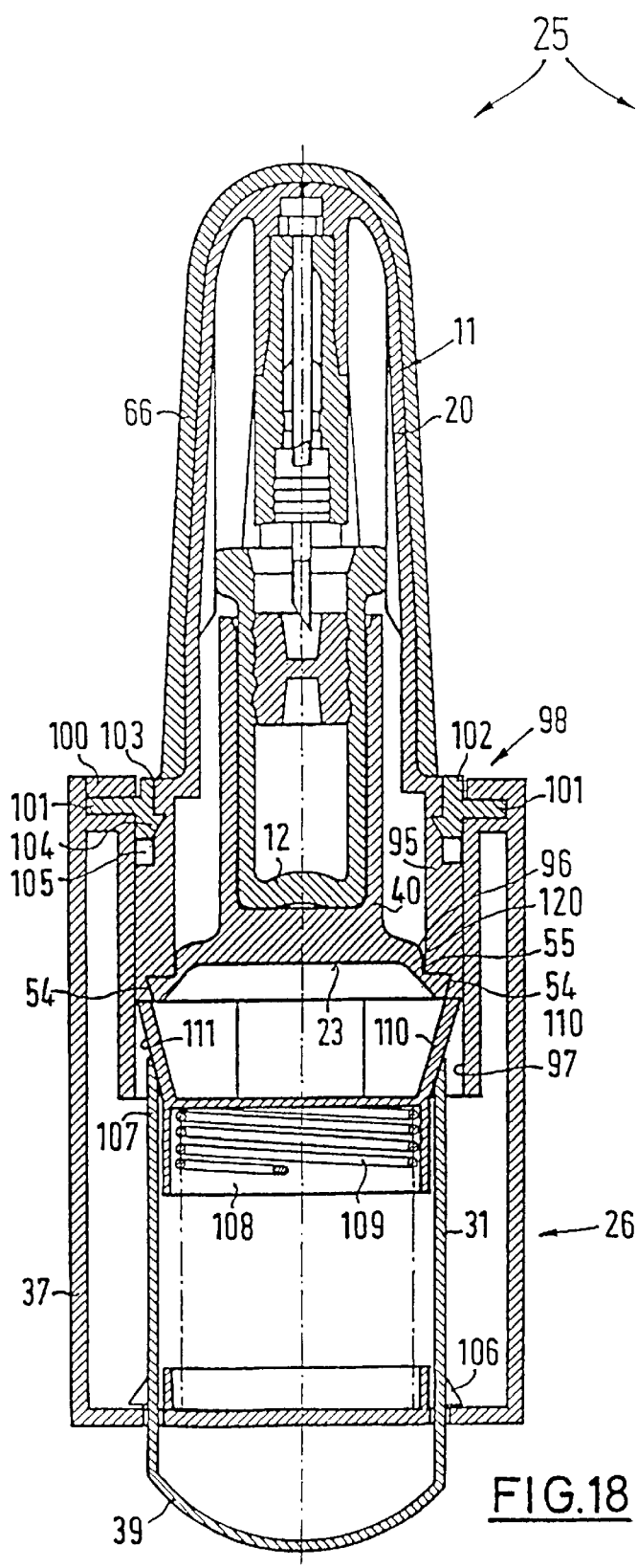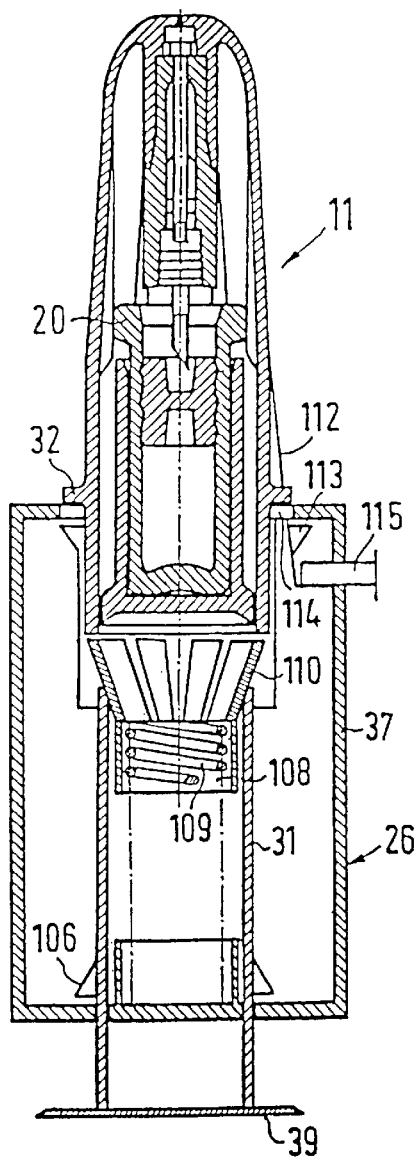
FIG.18
FIG.19

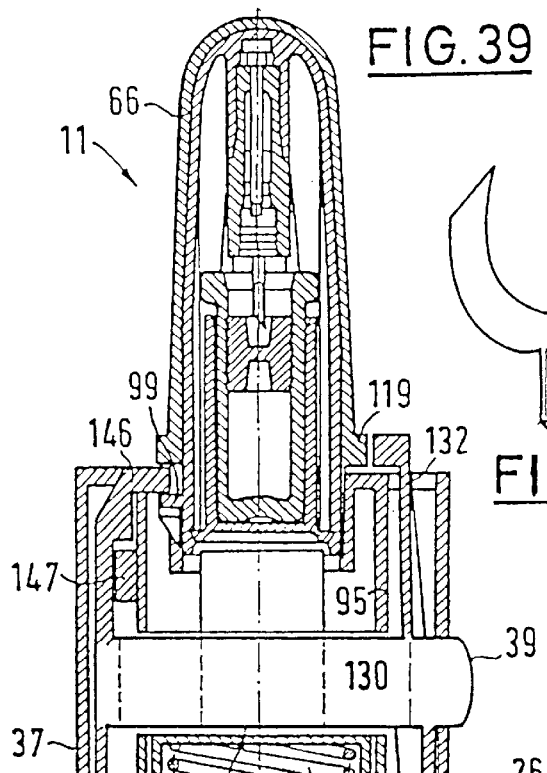
FIG. 39
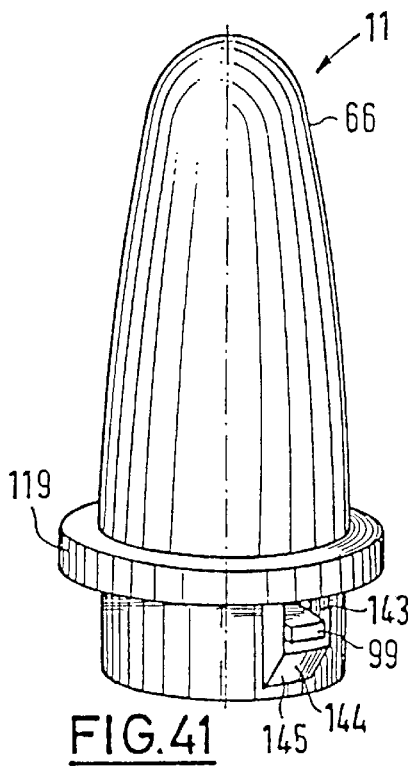
FIG. 39a
FIG. 41
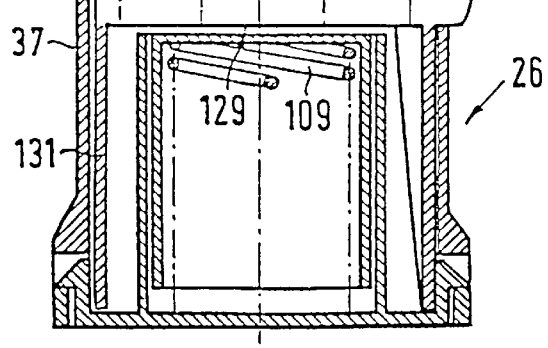
FIG. 40
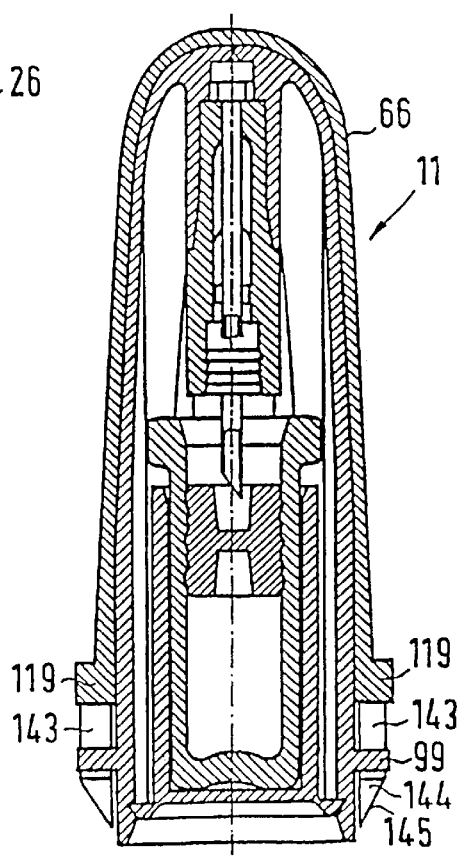
FIG. 42

DISPENSER FOR FLOWABLE MEDIA

During the discharge, particularly the atomization of pharmaceutical or cosmetic products, problems frequently arise, which are caused from the need for very precise dosing or the perishability or contamination susceptibility of the products once the media containers have been opened, dirtying or contamination risks in the line paths, etc. Thus, disposable dispensers have been developed, which contain the product in a medium container forming at the same time the pump cylinder for a thrust piston pump and which following the initial opening of said container, e.g. through a needle piercing the piston-type stopper, the content can be discharged in one or more strokes. Such an atomizer is described in WO 96/24439.

After use the entire dispenser is disposed of. The object of the invention is to obviate this. This is achieved by the solution described in the description and claims and shown in the drawings.

The invention in particular creates a dispenser, which has a dispenser unit easily replaceable by the user and which is connected to a reusable actuating unit for use purposes and can subsequently be separated again, the actuating unit being reusable subsequently, whereas the dispenser unit is disposed of. The replaceable dispenser unit not only comprises, as in the case of DE 40 21 263 A, the pump chamber and its closure, but also makes it possible to replace all parts coming into contact with the medium, i.e. the channel paths, the outlet opening and optionally the elements coming into contact with the body parts to be treated as a result of operation, e.g. a so-called nose connecting piece, i.e. a connection which is introduced into the nose and containing at its tip the outlet opening (spraying nozzle).

The invention provides numerous possibilities for implementing this. They are explained in the following description and the individual features, both singly and preferably in the form of subcombinations, can be implemented in an embodiment of the invention and are protectable as such and also in other fields.

Preferred embodiments of the invention are shown in the attached drawings, wherein represent:

FIG. 1 A longitudinal section through a dispenser unit.

FIG. 2 A dispenser with a releasable spring actuation in part longitudinal section and the associated rechargeable dispenser unit.

FIG. 3 In part longitudinal section a dispenser and a longitudinal section through the associated replaceable dispenser unit.

FIGS. 4 & 5 Plan views of two versions of actuating units.

FIG. 6 A longitudinal sectional exploded view of a dispenser comprising a dispenser unit and actuating unit, with a detail.

FIGS. 7 to 11 In each case in longitudinal section embodiments of dispensers.

FIGS. 12 & 13 A part longitudinal section and a longitudinal section in two planes perpendicular to one another through a dispenser.

FIG. 14 A perspective view of the dispenser.

FIGS. 15 to 17 The dispenser according to FIGS. 12 to 14 in a corresponding representation in a second operating position.

FIGS. 18 & 19 Two longitudinal sections through embodiments of dispensers.

Figure 20:
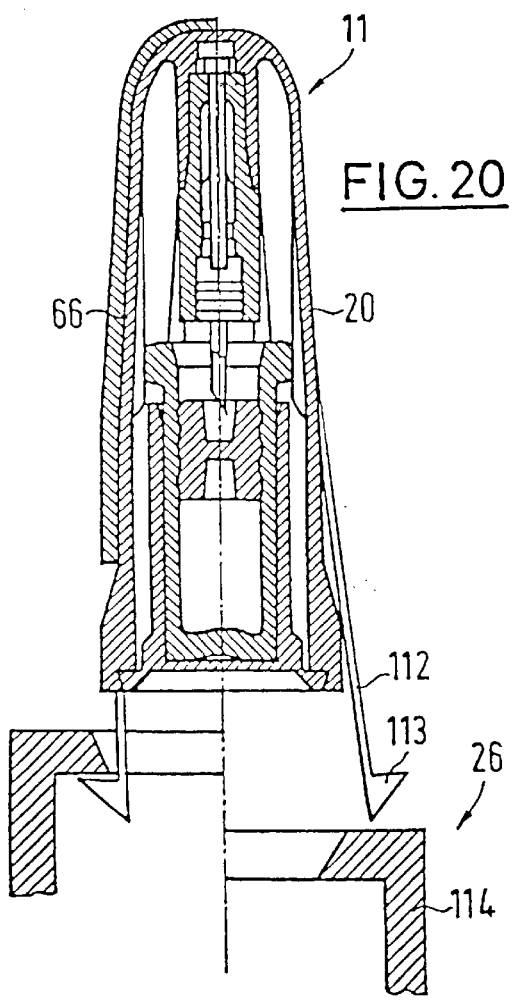

FIG. 20 A dispenser unit with intimated fastening to an actuating unit.

Figure 21:
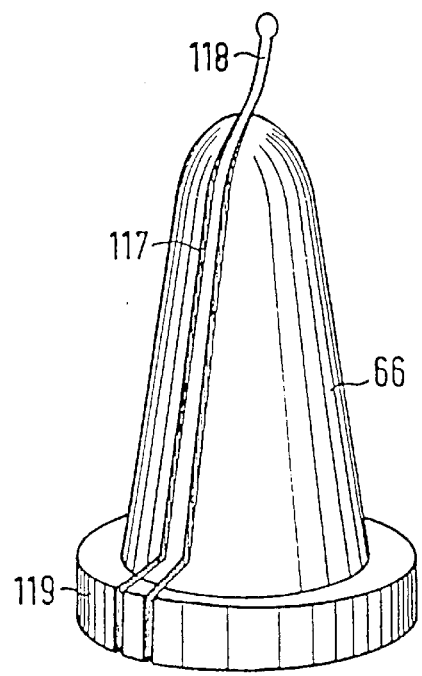

FIG. 21 The perspective view of a protective cap.

Figure 23:
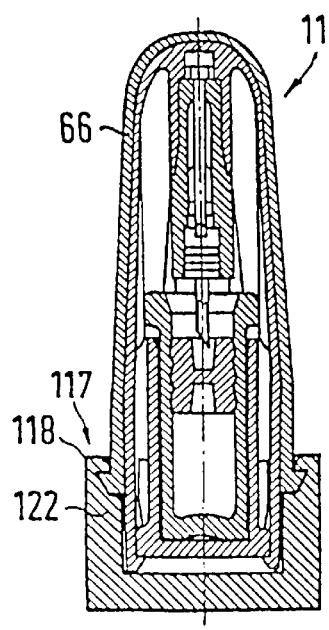
Figure 22:
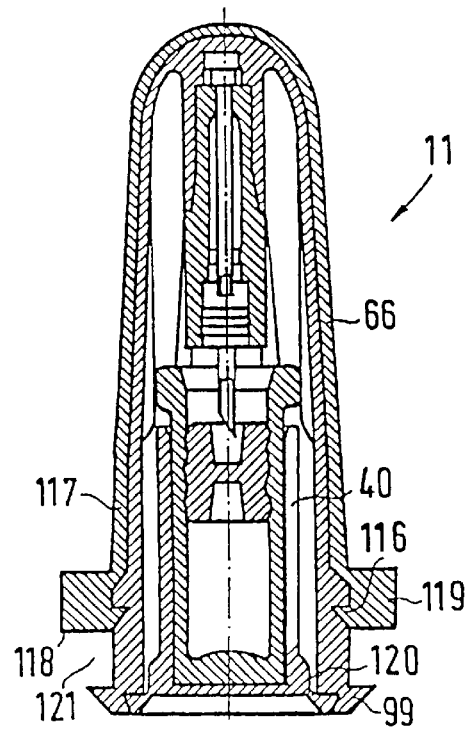
Figure 24:
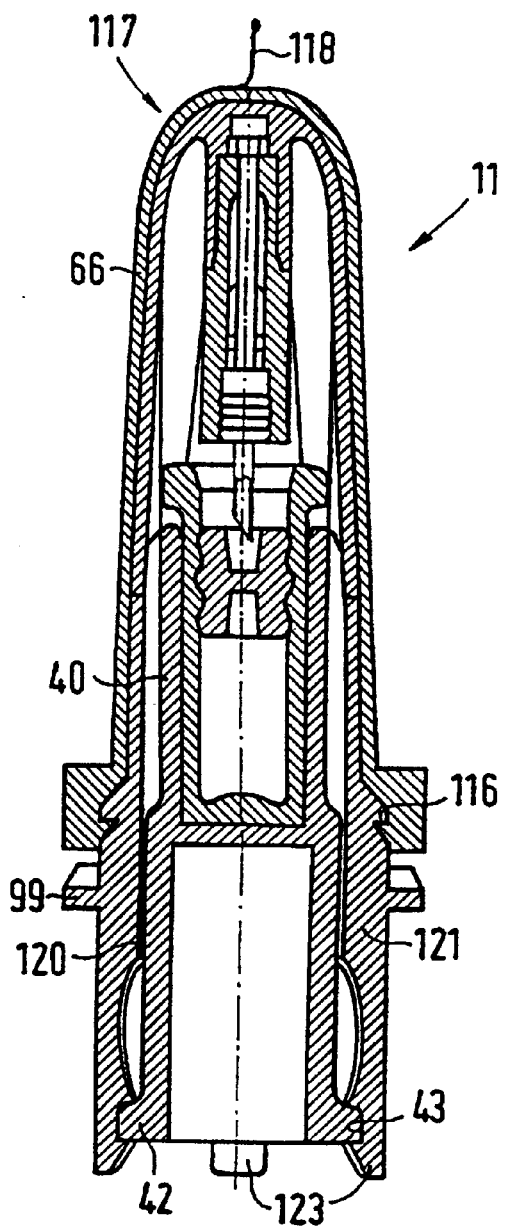

FIGS. 22 to 24 Longitudinal sections through rechargeable dispenser units.

Figure 25:
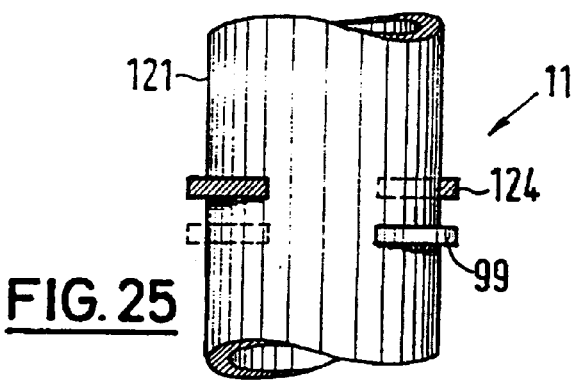
Figure 26:
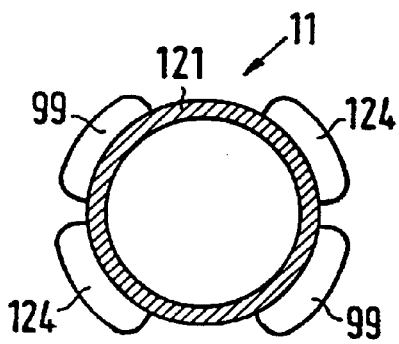
Figure 27:
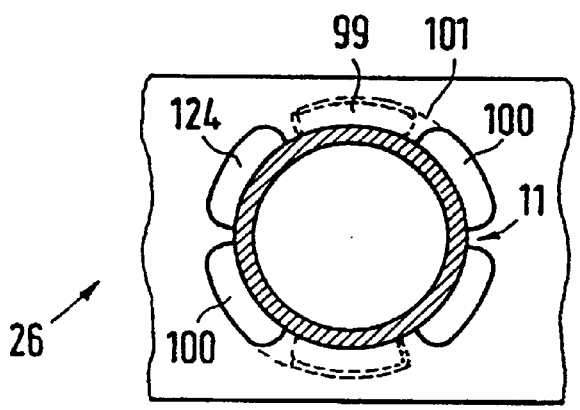

FIGS. 25 to 27 Diagrammatic representations of locking projections and their cooperation with the actuating unit.

Figure 28:
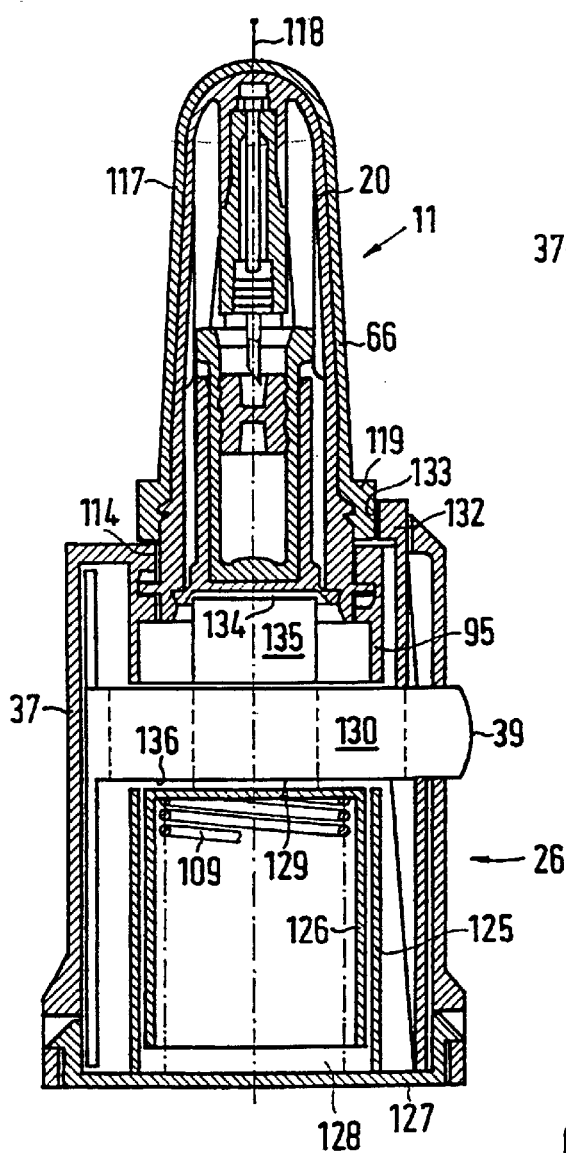

FIG. 28 A longitudinal section through a spring-actuated dispenser.

Figure 29:
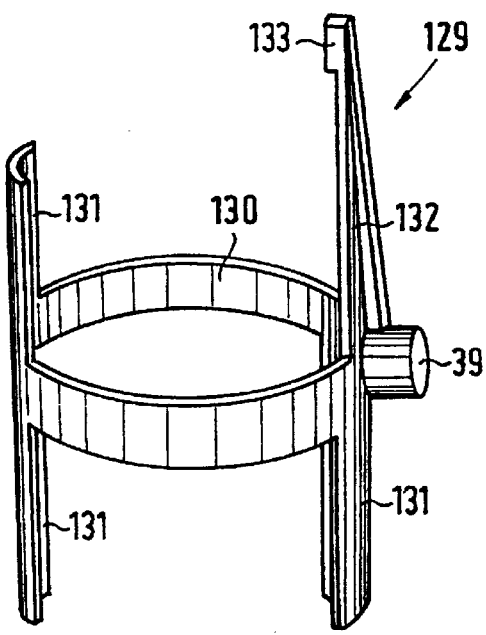

FIG. 29 The perspective view of a release element for the same.

Figure 30:
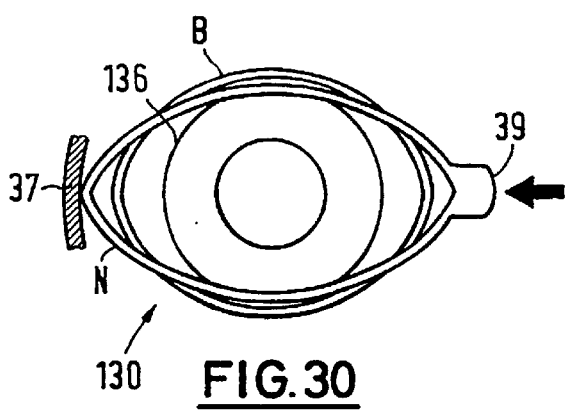

FIG. 30 A diagrammatic representation of the operation of the release element.

Figure 31:
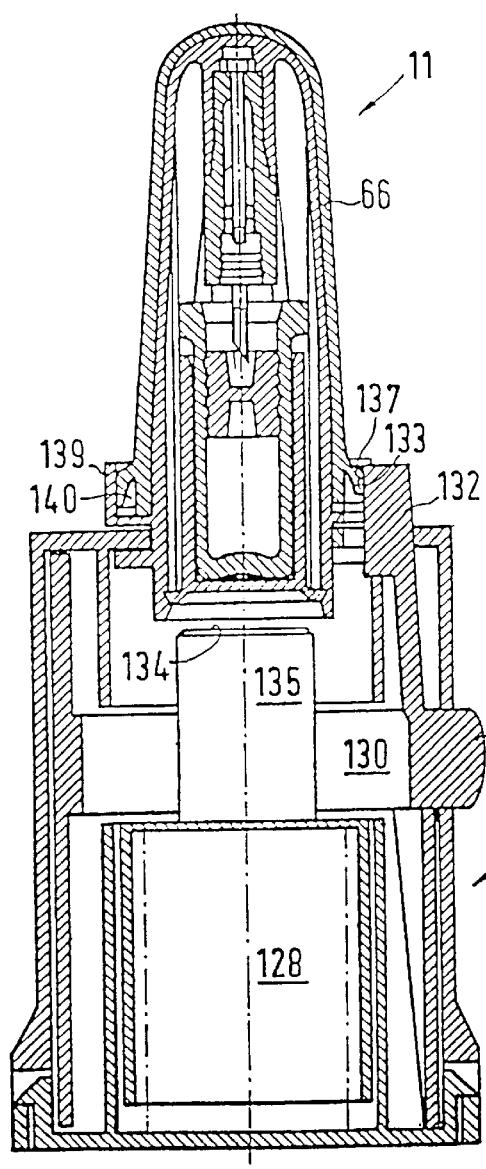

FIG. 31 A longitudinal section through a dispenser.

Figure 32:
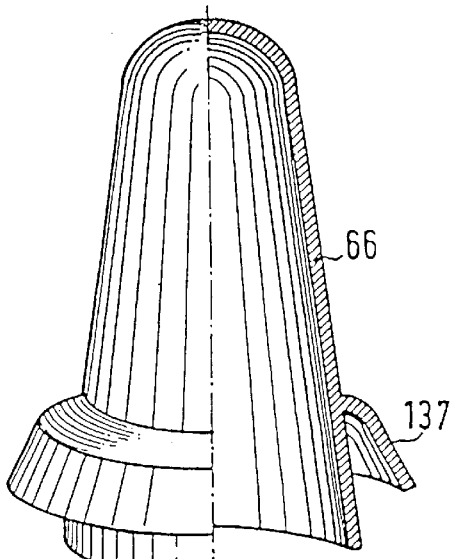
Figure 33:
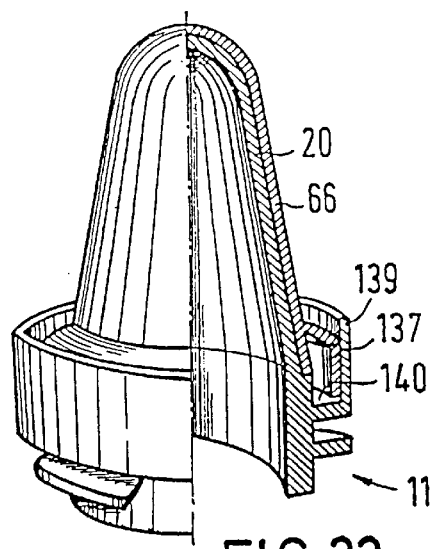

FIGS. 32 & 33 In perspective, part sectional view an embodiment of a protective cap.

Figure 34:
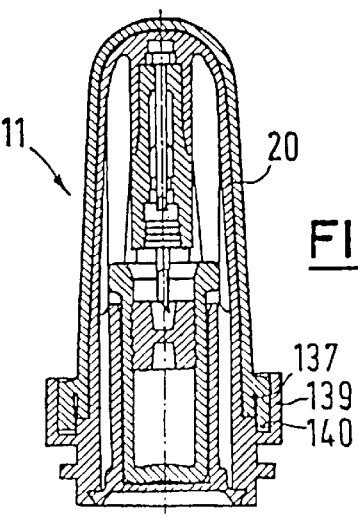

FIG. 34 A longitudinal section through the protective cap with dispenser unit illustrated by FIGS. 32 and 33.

Figure 35:
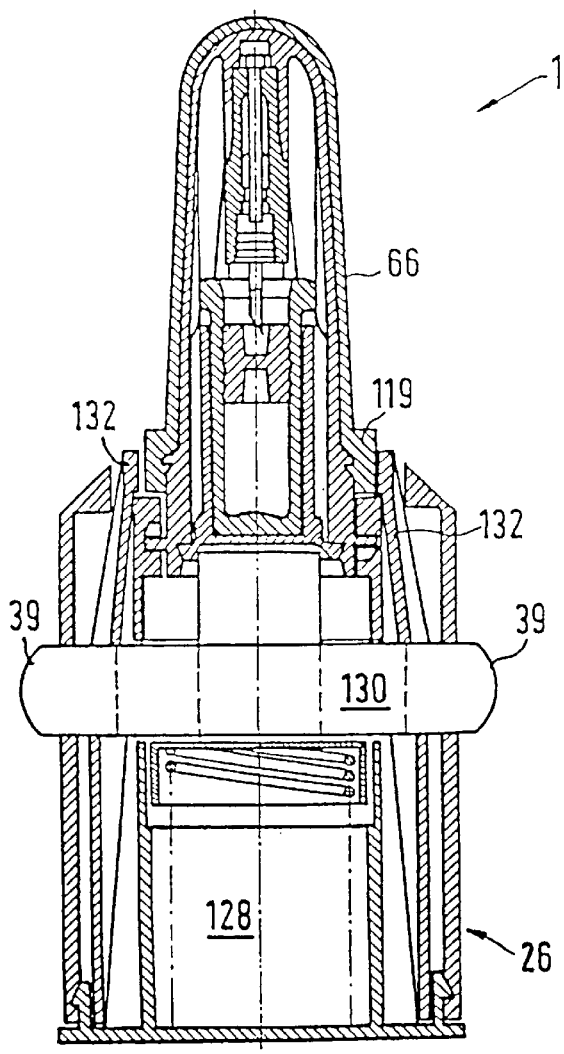

FIG. 35 A longitudinal section through a dispenser.

Figure 36:
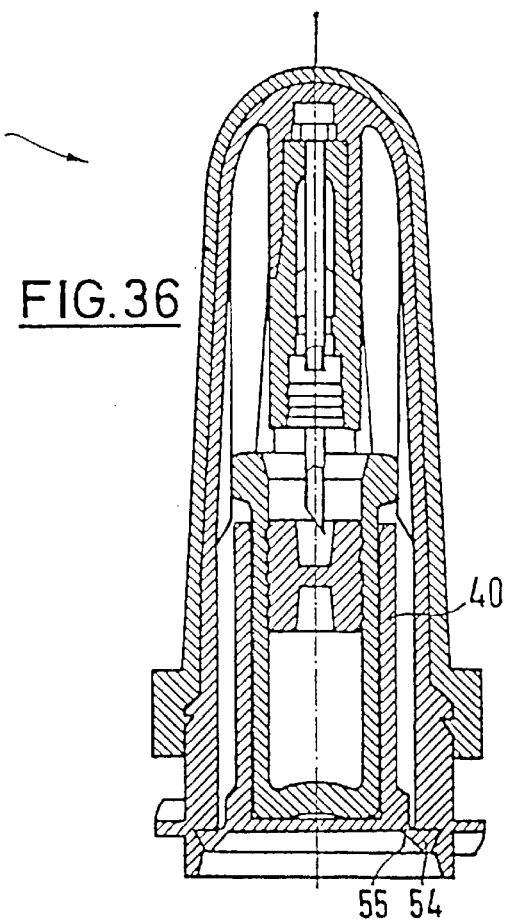
Figure 37:
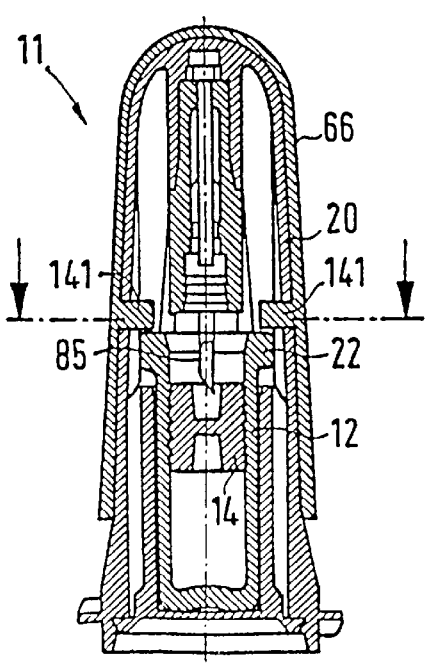

FIGS. 36 & 37 Longitudinal sections through rechargeable dispenser units.

Figure 38:
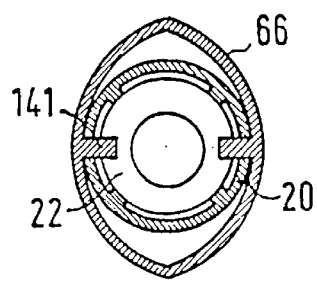

FIG. 38 A section along line I—I in FIG. 37.

FIG. 39 A longitudinal section through a dispenser unit.

FIG. 39a A detail from FIG. 39 in plan view.

FIG. 40 A perspective representation of a dispenser.

FIG. 41 A dispenser unit covered by a protective cap.

FIG. 42 Said dispenser unit in longitudinal section.

Figure 43:
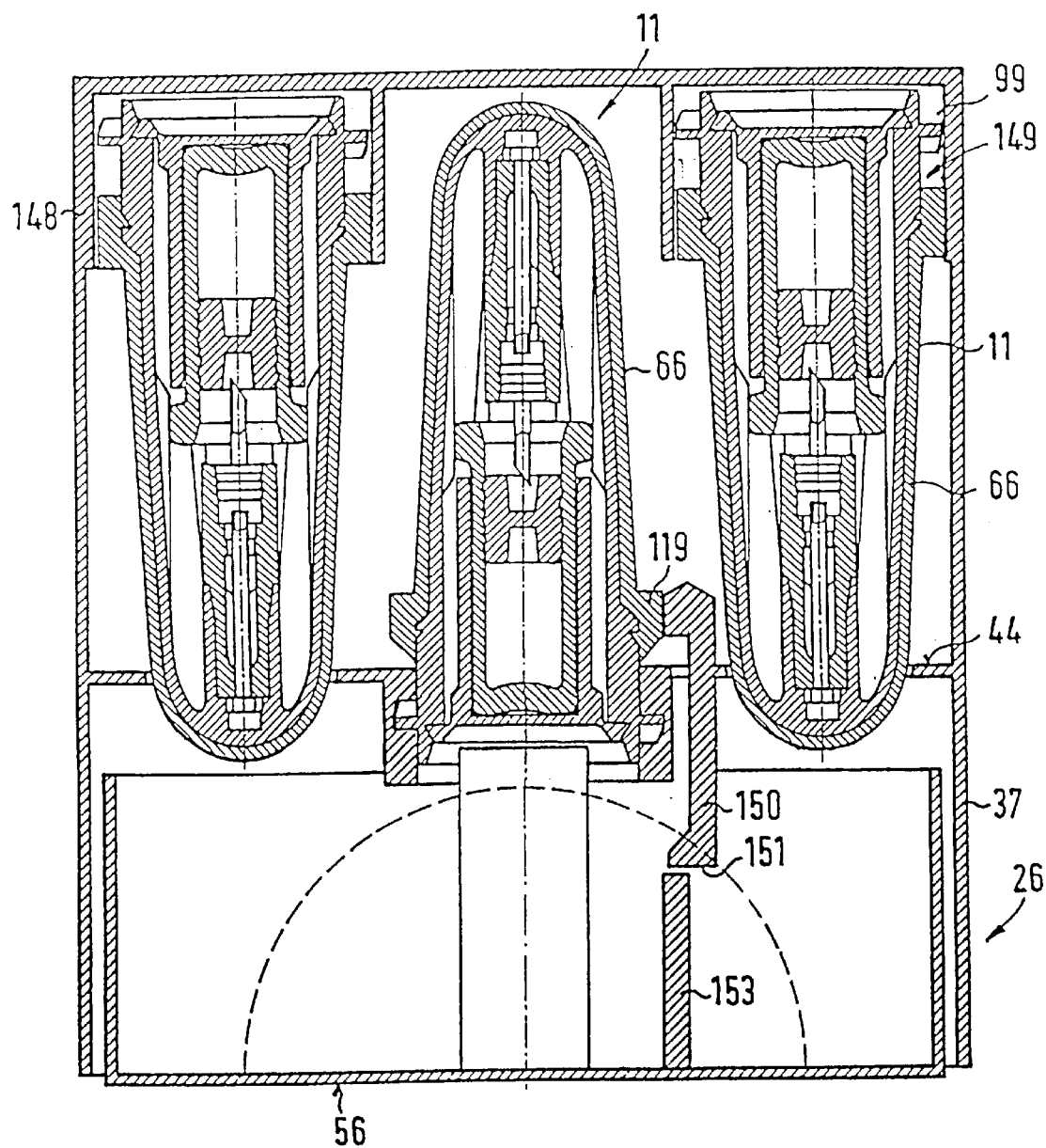

FIG. 43 A longitudinal section through a dispenser with reserve receptacle in the lid.

FIG. 1 shows a construction of the dispenser mechanism, such as is used in the following embodiments, it being described in detail solely by means of FIG. 1.

In the construction according to FIG. 1 it forms a dispenser unit 11 with a media container 12, which contains the medium to be discharged 13, e.g. a pharmaceutical or cosmetic liquid. The medium container is usually made from glass, if this is necessary due to the protection against diffusion and the compatibility of the material. It also forms a thrust piston pump chamber, whose piston is formed by a piston-like stopper 14, which tightly seals the only opening in the media container. It is made from a very elastic, usually rubber-like plastics material and has a relatively long generated surface, so as to have a reliable function in its piston function. Circumferential beads on the generated surface ensure the sealing action and controlled resistance conditions during axial movement. Central recesses formed from either side in the middle defines a piercing area 15 of reduced thickness, which can be pierced by a hollow needle 16 similar to a hypodermic needle. This is received, optionally by means of a pressed-on retaining bush 17 in a piston-type push rod 18 and extends through the central opening of said push rod 18 to just upstream of an atomizing nozzle, which forms the outlet opening 19. It is provided in an outlet connection 20, which as a forwardly rounded projection envelops most of the dispenser unit and receives the piston-type push rod inserted therein or connected in one piece therewith. The piston-type push rod 18 defines with the inner area of the outlet opening an angular momentum chamber 21, which permits an atomization in a spray cone, because the liquid is exposed there to angular momentum. The outlet connection has at its lower, open end face in FIG. 1 and outer flange 32.

By means of the outer flange 22 provided in the opening area, the media container leads into the interior of the outlet connection by means of inner guide webs 82.

The dispenser unit operates in the following way. If the media container 12 moves in the direction of the outlet opening, e.g. by pressure on its bottom surface 23, the hollow needle 16 firstly pierces the piercing area 15 of the piston-type stopper 14. Shortly thereafter the end face 24 of the push rod 18 reaches the upper end face of the piston-type stopper 14 and presses the latter downwards. The medium 13 passes out through the inner channel 85 of the hollow needle, which forms the outlet channel and leads to just upstream of the outlet opening 19. There the liquid passes into the angular momentum chamber 21 and then, with the associated angular momentum, passes out of the outlet nozzle 19 as a spray cone in finely atomized form. When the piston-type stopper 14 strikes against the bottom of the media container, the discharge stroke is at an end. However, it is also possible by means of interposed obstacles, e.g. an intermediate stop, which can be overcome or obviated by a separate actuation, to provide a multistage stroke. This is e.g. described in WO 96/24439, to which reference is made here. All the dispenser units described within the scope of the present invention can be constructed with a single or multiple stroke, even though preference is given to the construction as a disposable atomizer.

FIG. 2 shows a dispenser 25 using a dispenser unit 11 according to FIG. 1. Its actuating unit 26 is in the form of an elongated, cylindrical pin or stick, at whose one end face, the upper one in FIG. 2, is provided a reception or charging opening 27 for the dispenser unit 11. It is inserted through a charging cutout 28 into a charging chamber 29, after the prior retraction downwards out of the charging chamber of an actuating ram 30, which is guided in an actuating sleeve 31. The dispenser unit shown in broken line form engages with the opening-side outer flange 32 of the outlet connection 20 in the edge region of the reception opening 27.

In the portion of the actuating unit 26 following on to the charging chamber is provided a rotary mechanism, which is actuated by a rotary knob or button 33 at the lower end. In much the same way as with a lipstick mechanism, the actuating sleeve 31, is retracted e.g. by means of a coarse thread 34 or is moved in the direction of the inserted dispenser unit 11. When the head 34 of the actuating ram 30 reaches the bottom 23 of the media container 12, the latter is guided through a corresponding recess of the head. However, simultaneously by means of a release detent 35 the actuating ram is fixed in the position shown in FIG. 2. The further upwards-sliding sleeve 31 compresses a spring 36 and pretensions it for a later actuating stroke. This position is shown in FIG. 2.

The actuating detent is released from the wall of the actuating unit casing 37 by corresponding U-shaped cutouts, lateral connecting webs 38 forming a type of resilient swivel joint. Consequently the release detent together with a release button provided on the other side of the connecting web 38 and also separated from the wall by a U-shaped cutout, forms a two-armed lever.

If the user presses on the release button 39, it swings inwards and the release detent 35 outwards (see arrows). The actuating ram 30 is released, the spring 36 presses the media container 12 upwards and in this way brings about the discharge stroke.

Following actuation by a corresponding rotation of the rotary button or knob 33 the actuating ram and actuating sleeve are moved back again, so that the charging chamber becomes free. The spent dispenser unit can be removed through the charging opening 28 and replaced by a new one, as is intimated in FIG. 2. It is also shown that e.g. in the rotary button 33 can be formed a reserve chamber for a dispenser unit 11.

Admittedly DE 40 15 367 A already discloses dispensers, which operate with spring pretension and release, but here a very attractive device has been created with a high degree of operational automation, although the dispenser unit is in fact a disposable unit. This is particularly important for medicaments against highly painful illness phenomena, such as e.g. migraine, where a corresponding preparation to be received via the skin (nasal mucosa) is always kept by the patient in a ready to use form and must be easy to administer by the latter, because his or her functions can be impeded by the severe pains. The dispenser can be very easily carried and handled in the form of a stick and need not be much larger than a fountain pen. The actuation of the pump by spring tension ensures a predetermined actuating force.

FIG. 3 shows a particularly simple, easily manufacturable construction, in which a dispenser unit 11 is provided, which has two outer flanges 32 on the outlet connection 20. The media container 12 is received in a reception sleeve 40 which, like all parts of the presently described atomizer, except for the ampoule, hollow needle and springs, can be made from a plastic injection moulding.

Said sleeve 40, whose interior supports on webs 41 the media container, is provided on its outside with an annular projection or flange 42, which cooperates with a recess 43 on the inner circumference of the outlet connection 20. The two form a locking connection which can be overcome by axial pressure and which as a result of a one-sided, barb-like, bevelling of the flange 42 on the top surface, as can be seen in FIG. 3, can be more easily overcome in the compression direction than in the opposite direction. Thus, an actuating pressure point is created, which requires a specific minimum actuating force to overcome the same. It is thereby ensured that actuation takes place speedily and without any possible intermediate stop, which could impair atomization. Such a pressure point, whose function is described in detail in WO 96/24439, is provided in all the versions described hereinafter.

FIG. 3 shows that the dispenser unit 11 can be placed in an actuating unit 26, which in the present case comprises a base casing part 37 having a flat oval shape (cf. FIGS. 4 and 5). To the charging opening 27 are connected lateral actuating shoulders or faces 44. From the same passes round an oval jacket 45, but which in its two flatter side faces has finger cutouts 46. Thus, the portion of the reception and actuating sleeve 40 located in said part is admittedly protected against accidental actuation, but is accessible for a thumb for actuation purposes.

FIGS. 4 and 5 show two possibilities for joining together the dispenser unit and actuating unit 26. According to FIG. 4 the dispenser unit 11 is slid into the in this case laterally open charging opening 27, namely with the portion positioned between the two outer flanges 32. Locking projections 47 prevent the dropping out of the dispenser unit, whilst the two outer flanges 32 together with a neck 48 of the charging opening have an axially securing action.

According to FIG. 5 the casing 37 of the actuating unit 26 is hinged. It is admittedly manufactured as a one-piece plastics injection moulding, but can be flapped up by means of a film hinge 49 and a separation point 50 (cf. arrows in FIG. 5). The dispenser unit 11 is inserted in the charging opening 28 in the opened state of the casing 37 and then the latter is closed again, a locking connection 51 being provided at the separation point 50.

Actuation takes place manually in that the operator in each case places one finger on each of the actuating shoulders on either side of the outlet connection 20 and with the thumb presses upwards the reception sleeve 40.

Subsequently by unlocking (FIG. 4) or unflapping up of the casing (FIG. 5), the dispenser unit can be ejected and disposed of. The part which is to be used again, i.e. the actuating unit 26, is admittedly here only shown as a one-piece plastics part, but from the area and optionally also volume standpoint is the largest part, so that its reuse is worthwhile. In addition, the packing and transportation volume of a treatment unit comprising several dispenser units is made much smaller, which is particularly important for patients, who always have to carry several dispenser units with them.

FIG. 6 shows a similar construction in which the actuating unit 26 and its casing 37 correspond to the basic shape shown in FIGS. 3 to 5. However, here the charging opening 27 is in the form of a longer neck 48, on whose top is provided on the inside a circumferential locking groove 42 and cooperates with a corresponding, sloping locking projection 53 on the dispenser unit 11. The latter is externally provided on a ring 54, which is injection moulded in one piece with the reception sleeve 40, but is only connected by thin material bridges 55. The latter form a preset breaking point, which create the previously described pressure point function and also ensure that the product is tamperproof. The ring is inserted from below in a recess in the lower end face of the outlet connection 20 (cf. detail in FIG. 6).

As shown in FIG. 6, the dispenser unit and actuating unit 11, 26 are assembled. The dispenser unit with its reception sleeve 40 is firstly introduced from above into the charging opening 27. The locking projections 53 lock in the locking recesses 52 and secure the dispenser unit there.

By pressure with the thumb on the bottom surface of the reception sleeve 40 the dispenser is operated. As in the case of FIG. 3 it is firstly necessary to overcome the pressure point (in FIG. 3 by unlocking the snap connection 42, 43 and in FIG. 6 by destroying the material bridges 55 forming a preset breaking point). With the resulting, predetermined minimum actuating force the dispenser is now operated. Following use, as a function of the construction of the locking recesses and projections, the dispenser unit is either removed upwards again or can be pressed through downwards, in order to free the actuating unit 26 for a new charge.

Instead of the described locking connection, it is also possible to have a stopping or locking action through a type of bayonet catch between the dispenser unit and actuating unit and a similar effect will be described hereinafter. It is clear that through the relatively high neck 48 the outlet connection 20 can be made relatively short. It can be limited to the part exposed to body contact, whereas that part located between the two fingers of the user remains on the reusable casing 37 of the actuating unit 26, which saves dispenser unit material.

In the construction according to FIG. 7 use is made of a dispenser unit according to FIG. 1, i.e. without a reception sleeve 40. It is inserted in the charging opening 28 of the casing 37 of the actuating unit 26 either through a bayonet catch or from below. In the oval, lower opening of the casing 37 is located a pusher 56, which largely covers said lower opening and forms with the lower face 57 an actuating face. It is guided with lateral, upwardly directed wall parts 58 within the jacket 45 and engages with top bevelled projections 59 in opening 60 in jacket 45. A hollow central connection 61 whose function corresponds to the reception sleeve 40 supports the bottom 20 of the medium container 12.

For the insertion of the dispenser unit the latter, in the case of a construction with a bayonet catch, is introduced from above into the charging opening 27 and locked by turning. The media container rests on the reception connection 61 and is centred thereon by means of a conical reception opening.

For actuation purposes pressing takes place on the bottom face 57 until the locking devices 59, 60 free the pusher for upward movement. The reception connection 61 presses the media container 12 upwards and actuates the dispenser. The dispenser unit 11 can then be removed upwards again by means of the bayonet catch.

However, it is also possible here to construct the locking connection 59, 60 in such a way that the locking device 59 is freed from the opening 60 for ejection purposes, e.g. by pressure on the two flat sides of the oval casing 37, so that the pusher 56 can be extracted downwards. In this case the outlet connection 20 of the dispenser unit 11 only requires the outer flange 32 shown in FIG. 1 for engagement on the lower edge of the charging opening 28. It would then be possible to insert the dispenser unit from below together with the pusher 56 and then remove it again correspondingly.

It is also possible to provide a spring in the interior of the actuating unit, i.e. between the actuating shoulders 44 and the inner face of the pusher bottom 57, which moves back into the initial position said pusher 56 following actuation.

Figure 8:
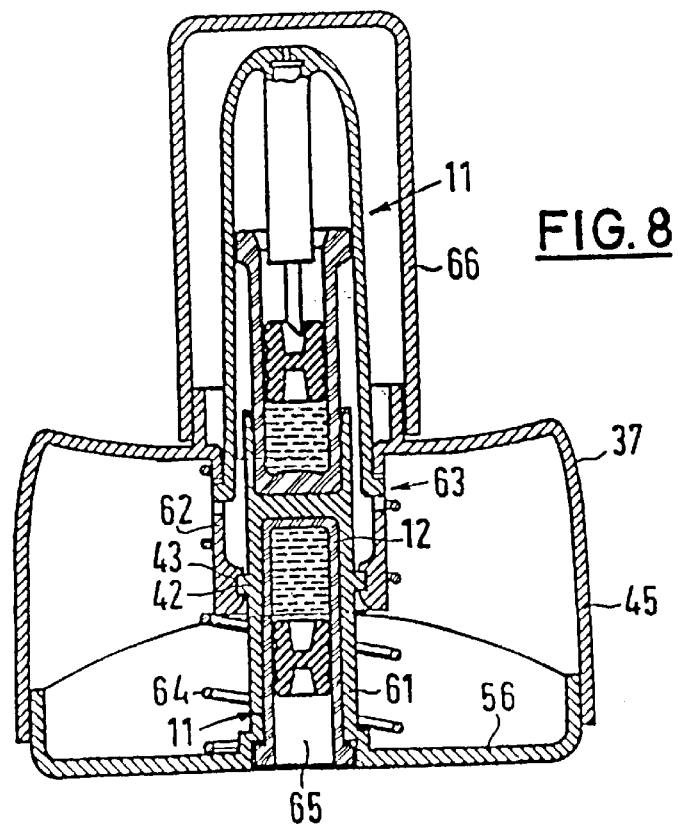

This is shown in similar form in FIG. 8 where, in place of the outer locking devices 59, 60 in FIG. 7, there is a pressure point-forming locking means 42, 43 between the reception connection 61 of the pusher and an inner connection 62, surrounding the reception connection 20, of the casing 37. Said connection could also be formed solely by webs or fingers, which would further assist the resilient locking function. The dispenser unit 11 is inserted by means of a bayonet joint 62 from above. Spring 64 ensures its return into the initial position shown in FIG. 8, following actuation.

The reception connection 61 contains a reserve chamber 65 for a dispenser unit 11. In this construction merely the media container with its piston-type stopper 14 would have to be replaced, following the removal of the outlet connection 20 together with the needle, piston-type stopper and outlet opening per bayonet. Such a construction is appropriate if there is no need to fear contamination or dirtying of the medium outlet paths. The construction according to FIG. 7 would also permit this. The locking connection 42, 43 ensures the pressure point function and the hold of the pusher unit on casing 37.

FIG. 8 shows a protective cap 66 helping to ensure that the medium outlet paths are protected against contamination, dirtying and drying out, so that said dispenser unit part could belong to the reusable actuating unit.

FIG. 9 shows a construction in which with a configuration otherwise similar to FIG. 7, the dispenser unit 11 inserted by bayonet 63 is closed on its underside by a product protection cap 67. It engages on the bottom of the media container 12, is guided in the interior of the outlet connection and rests on its lower edge with a ring 54 (cf. detail), which is extruded via destructible material bridges 55 to the product protection cap 67. The pusher 56 is fixed in the opening 60 by means of the barb-like locking projections 59, which extends upwards in slot-like manner into the jacket 45, so as not to impede an upward movement of the pusher 56 and so as not to take over the function of the actuating pressure point. This is in fact taken over by the material bridges 55, which are destroyed during actuation, if the central connection 61 of the pusher presses against the bottom of the product protection cap 67 and actuates the dispenser, accompanied by the interposing of said cap.

This construction has the advantage that the dispenser unit 11 forms a completely closed unit, because the wall of the outlet connection 20, which projects into the casing 37 and which is drawn down over the media container and the product protection cap 67 sealing the lower opening entirely surround the media container and its channel paths. If e.g. the outlet opening 19 is also provided with a tear-off or adhesive closure or seal, no contamination can arise when handling the dispenser unit.

FIG. 10 shows a construction in which the dispenser unit 11 inserted by means of a bayonet 63 into the charging opening 27 of the casing 37 is provided with a reception sleeve 40, which has extruded onto its outside by means of corresponding material bridges 55 the preset breaking ring 54. It cooperates with the outlet connection end face extended into the casing interior if there is pressure on the lower end face of the reception sleeve 40. The ring 54 then tears off and frees the stroke with the intended minimum actuating force.

FIG. 11 shows a construction in which the dispenser unit 11 corresponds to that according to FIG. 9 and is also inserted by a bayonet 63 into the casing 37 of the actuating unit 26. However, the lower face of the product protection cap 67 has an optionally spherical segmental shape on which presses an actuating ram 68 of the casing. The latter is part of an actuating lever 69 extruded on one side onto the actuating shoulders 44 by means of a film hinge 70. It is guided with its outer lever end 71 in a slot 60 of the jacket 45 of casing 37. In the case of pressure on the lower actuating face 57 the lever pivots clockwise about its film hinge 70 and the actuating ram 68 presses against the spherical segmental surface 72 of the product protection cap 67, tears off the preset breaking ring 54 and actuates the dispenser. A plastic tongue 73 extruded onto the lever portion 69 blocks the film hinge in the position shown by the lever end 71 and slot 60, so that the lever portion forms an optionally pretensioned plastic spring in one piece with the casing 37. With this construction by means of a certain lever action and by a resilient construction of the lever 69, a particularly effective, sudden actuation of the dispenser and the return thereof can be obtained.

In the construction according to FIGS. 12 to 17 a dispenser 25, whose dispenser unit 11 is shaped onto the outlet connection 20, has the actuating shoulders 44 constructed in the manner of an oval, inverted pan and only having a relatively short, downwardly directed jacket 45. The latter has inside circumferential locking projections 75, which cooperate with corresponding projections 76 on the actuating unit 26. The actuating shoulders in this way engage over the cross-sectionally oval shaped body 37 of the actuating unit 36 so as to give a continuous, smooth wall continuing on from the jacket 45. However, following onto the jacket 45 a retaining ring 78 is interposed and is either constructed as a separate part or, preferably, can be shaped by means of tear-off material bridges onto the jacket 45. It has a tear-off tongue 79 and is separable at this point by means of destructible material bridges. The body or base casing 37 of the actuating unit 26 are constructed in similar manner to a hollow tube having an oval cross-section. By means of cooperating detents 80, 81 an actuating body or pusher 82 is held therein, which in cross-section corresponds to the inside cross-section of body 37 and has on its underside an actuating face 57, which is accessible for the thumb of the user over the pump lift through an actuating cutout 46 in the body 37.

The actuating body 82 is centrally provided with an e.g. tubular actuating ram 30. On either side alongside the same or surrounding the actuating ram, starting from the actuating face 57, an unlocking element 83 is shaped to the actuating body 82 and is provided on its top with a step-like unlocking face 84, in whose extension face one another two unlocking tongues 85 of a protective cap 66 surrounding the outlet connection 20. They engage through openings 86 in the actuating shoulders 44 in the interior of the actuating unit 26 and are fixed by means of barb-like projections 87 in the interior of the actuating shoulders on the dispenser unit 11. The lower edge of the unlocking tongues 85 has an insertion inclined surface 88.

Through flange 42 and recess 44, the dispenser unit 11 has a pressure point-snap function, as described relative to FIG. 3. The recesses 43 can be provided on individual webs projecting from the underside of the actuating shoulders and which surround the reception sleeve 40 in crown-like manner.

The function is as follows. On installation all parts are fixed by mutual snapping in. The actuating unit can be delivered separately from the dispenser unit and kept ready, whereas the dispenser unit, including the retaining ring 78 is stored, fitted and subsequently removed separately. Fitting takes place by the locking in of the locking projections 75, 76, which can also be provided in the form of individual lugs on the circumference. FIG. 12 shows that they lock in, but the retaining ring 78 prevents the actuating shoulder with its jacket 45 from being completely pressed down onto the body 37 or the shoulders 89 formed by the same in the vicinity of a circumferential recess.

The unlocking tongue 85 with its barbs 87 secures the protective cap on the dispenser unit 11 so as to prevent accidental removal thereof. In this position shown in FIGS. 12 to 14, the dispenser 25 is secured against actuation. If a user presses on the actuating face 57, then the upper step 90 of the unlocking face 84 strikes the unlocking tongue 90 and prevents the actuating ram 30 from reaching the bottom surface 23 of the reception sleeve 40 or the exertion of an actuating pressure thereon.

For unlocking purposes and consequently for the preparation of actuation release, the user must tear off the retaining ring 78 by means of the tear-off tongue 79. Then, as shown in FIGS. 15 to 17, the dispenser unit can be correspondingly moved up to the actuating unit 26, so that then the end face of the jacket 45 rests on the shoulder 89. By means of the inclined face 88, the step 90 of unlocking element 83 presses outwards the unlocking tongue 85 of the protective cap 66, the latter being flexibly outwardly pivoted about its fixing point 91 to the circumferential jacket of the protective cap 66. In this position, if the barb 87 in conjunction with the opening 86 is designed in such a way that through the pivoting action they can become free from one another, the protective cap 66 can be manually removed. Thus, i.e. only following the removal of the protective cap, the dispenser is ready to operate and can now be operated by pressure on the actuating face 57 in the manner described hereinbefore for atomizing the liquid 13 contained in the media container 12, following the application of the minimum actuating pressure ensured by the pressure point means 42, 43.

In order to additionally prevent actuation taking place prior to the removal of the protective cap, by a corresponding construction of the barb 87 and opening 86, it is also possible to provide that even after the pivoting out of the unlocking tongues 85, whereof several can be provided on the circumference, the protective cap can still not be completely removed. According to this embodiment it would be necessary for the user by lateral pressure on the protective cap 66 to split it lengthwise, which is made possible by a gap 92 in a pot or cup flange 93 and a break-open line 94, intimated in FIG. 17 and brought about by weakening the jacket of the protective cap 66.

Thus, the protective cap would only be freed through openings and barbs 86, 87 following the breaking open of said cap. The user can then remove it and can only then use the dispenser. This ensures that the dispenser is not operated when unlocked and with the protective cap still fitted and through the destruction of the cap it is also indicated that a use has already taken place even if the user subsequently places said cap back on the dispenser unit which, after use, has been drawn off from the actuating unit, overcoming the locking projections 75, 76, and disposed of.

In the dispenser 25 according to FIG. 18 the pressure point securing means of the dispenser unit 11 is provided the construction described relative to FIG. 6 with a tear-off ring 54 and with material bridges 55 serving as a preset breaking point. The casing of the dispenser unit 11 also incorporating the outlet connection 20 has a downwardly directed, tubular projection 95, in which is relatively tightly guided an outwardly directed flange 96 of the reception sleeve, on which are also provided the destructible material bridges and consequently a penetration of dirt into the interior of the dispenser unit is prevented. Thus, as from the sealing action, the resulting narrow gap 120 exerts its effect.

The projection 95 is inserted in a cylindrical pipe socket 97 of the actuating unit 26 and is fixed on the top by a combination of bayonet and screw thread 98. This can also be seen in FIG. 24 and contains wing-like, projecting locking elements 99, inclined corresponding to a screw thread, which are inserted from above through cutouts 100 in the casing 37 of actuating unit 26 and which can then be turned into thread-like, tilting recesses 101 up to a stop member. This type of combined bayonet and screw connection, in the case of rapid, uncomplicated usability, ensures a firm, positive and non-positive connection.

The wing-like locking elements 99 are provided on a ring 102, which is shaped onto the protective cap 66 by means of destructible material bridges 103. It has on its inside barb-like locking devices 104, which engage in a projection 95 of the dispenser unit and prevent an upward drawing off of said ring. Optionally on the underside there are cooperating locking teeth 105 on ring 102 and projection 95, in order to prevent the turning of the ring 102 with respect to the dispenser unit 11 and so as to interconnect the two in non-rotary manner.

The actuating unit 26 is in the form of a pretensionable unit releasable by means of an actuating button or knob 39, as has already been explained relative to FIG. 2. For this purpose the casing 37 of the actuating unit 26 contains a sleeve 31, which at the bottom terminates in the actuating button 39 and which is arranged coaxially with the dispenser unit and is movable. It is so held by means of barb-like locking devices 106 in casing 37 that the actuating button 39 projects downwards somewhat, but is upwardly movable. In the sleeve 31 is guided a release element 107, which defines a cup-shaped recess 108, in which is supported a compression spring 109. The latter can either be supported on a lower casing wall 37 or in the release button 39 forming the bottom of the sleeve 31. On the top of the release element is provided an expanding or spreading element 110, which comprises individual, resilient, conically outwardly directed expanding tongues, which are supported on the underside of the annular projection 95 of the dispenser unit and are prevented by pipe sockets 97 from further conically expanding, because they are under the pressure of the compression spring 109. The sleeve 31 engages on the outer, inclined face 111 of the expanding element.

The function is as follows. The dispenser unit 11 is delivered as a replaceable element with protective cap 66. The latter is firmly connected to the dispenser unit by locking devices 104 and ring 102. On inserting the dispenser unit in the actuating unit 26, i.e. into the pipe socket 97, the lower face of the annular projection 95 acts on the expanding elements 110 and presses them, which previously stood further upwards in the pipe socket and could optionally be rendered loss-proof by an annular shoulder provided there, under the tension of the compression spring 109. The bayonet 98 locks in and is secured and tightened by the turning of the dispenser unit and actuating unit.

This can also be brought about in that, such as is e.g. known from the syringe commercially available under the trade name IMIGRAN, the actuating unit is pressed counter to the tensile force onto a storage container for the dispenser unit, which has a clamping plunger and secures the dispenser unit in a position permitting the securing thereof and insertion thereof by rotating the actuating unit.

Thus, the actuating unit is fixed. Prior to actuation the protective cap 66 is loosened and removed by rotation with respect to the actuating unit 26 and accompanied by the tearing off of the material bridges 103. If a pressure is now exerted on the release button 39, the sleeve 31 slides upwards and compresses the expanding element 110 until it slides inwards on the bevelled insides of the ring 54, strikes the face 23 of the reception sleeve 40 and actuates the dispenser under the pressure of the tensioned compression spring 109. When actuation has taken place, by rotating the outlet connection 12 with respect to the actuating unit 26, the dispenser unit 11 can be released and removed from its bayonet locking 98. The teeth or serrations 105, which cat be constructed similar to Hirth-type serrations, ensure the transfer of the rotary force to the bayonet ring 102.

As here the insertion of the dispenser unit takes place under spring tension, it can be advantageous to link the bayonet and/or screw connection with a snap connection, in that the bayonet or thread flank projections 99 are provided with a corresponding bevel and corresponding flexibility, so as to permit the locking thereof in correspondingly constructed threaded or bayonet recesses 101 without any specially provided recesses 100. If a screw component is contained, they can then be brought into their end position by further rotation. Unlocking takes place as for a bayonet or thread by rotation in the opposite direction and removal via a cutout 100.

It is also pointed out that the preset breaking ring 54 is so fixed by a corresponding undercut in projection 95 that the reception sleeve and therefore the media container 12 cannot be removed from the dispenser unit.

FIG. 19 shows a construction whose construction and function correspond to that of FIG. 18. However, the fixing of the dispenser unit 11 on the actuating unit 26 takes place by means of a resilient locking lever 112, which is shaped onto the dispenser unit casing and engages with a barb-like detent 113 behind the inside of the casing 37 of the actuating unit 26, after being inserted from above in the reception opening 114. A flange 32 on the outlet connection 20 forms an abutment for fixing purposes. For removing the dispenser unit after use, an ejector button 115, separate from the release button 39, is provided laterally on the jacket of the actuating unit.

FIG. 20 shows a construction in which the fixing of the dispenser unit 11 to the actuating unit 26 also takes place by means of locking levers 112 designed similar to spring legs, as well as corresponding barb-like detents 113. They are so shaped onto the casing wall of the dispenser unit 11, i.e. on the outlet connection 20, that they can be expanded further than corresponds to the opening cross-section of the reception opening 114 (FIG. 20, right-hand side). This prevents insertion. Only if the protective cap 66 is fitted (FIG. 20, left-hand side), does it compress the locking levers 112 to such an extent that they can engage in locking manner therein, optionally assisted by a bevel on the reception opening 114. This prevents the insertion of a dispenser unit in which the protective cap has already been removed, which in certain circumstances may have been used and/or contaminated. The release and/or ejection of the dispenser unit can take place in accordance with FIG. 19.

FIG. 21 shows a way of securing the protective cap. It is fixed to the dispenser unit, as shown in FIG. 22, with a barb-like back-snapping means 116. To remove the same it is necessary to separate it along its jacket. This takes place by means of a strip-like tear-up tongue 117, which is connected to the jacket from the inside or outside, but tightly in the non-torn-up state. A gripping tongue 118 for gripping and tearing up the protective cap 66 in the case of FIG. 21 projects at the upper, closed end of the protective cap. The tear-off tongue extends to a flange 119 projecting from the jacket (cf. also FIG. 22).

In FIG. 22 there is once again a strip-like tear-up tongue 117, but there the gripping tongue 118 is shaped in the vicinity of the flange 119. The tear-up tongue extends over the protective cap to the extent necessary for a completely satisfactory removal. It is generally sufficient to have a separation in the vicinity of flange 119, but it is also possible to draw the tear-up tongue entirely over the jacket.

FIG. 22 shows the locking mechanism of the dispenser unit 11 in an actuating unit explained relative to FIG. 18 using a snap/bayonet/screw locking element. 99 provided with a corresponding insertion bevel. As in FIG. 18, there is a very narrow gap 120 between the reception sleeve 40 and the casing 121 of the dispenser unit 11, which also incorporates the outlet connection 20, in order to bring about a sealing action.

In FIG. 23 the dispenser unit 11 constructed as rechargeable cartridge is covered by the protective cap 66 in the vicinity of its outlet connection 20 in the delivery state. It is held on the dispenser unit in that it is locked in unremovable manner in a closure cap 122, which covers and protects against dirt the otherwise open side of the dispenser unit 11 opposite to the outlet opening 19. The closure cap can only be opened by means of a tear-up tongue 117, 118, as described relative to FIGS. 21 and 22, so that the protective cap 66 can be removed. Only then is insertion in the actuating unit possible.

Also in the case of FIG. 24 a corresponding tear-up tongue or tear-up strip 117, 118 is provided in order to remove the protective cap, which is otherwise fixed by gripping teeth 116 on the dispenser unit casing 121. FIG. 24 shows the locking element 99 of bayonet 98 constructed in the manner of tilting wings and already explained by means of FIG. 18. However, they are directly provided on the dispenser unit casing 121 in the form of projecting segments. The pressure point function once again takes place by means of projections 42 on the reception sleeve 40 and recesses 43 provided on webs 123 projecting downwards from the casing 121 in crown-like manner. Once again there is a narrow, dust and dirt-proof gap 120 between the casing 121 and reception sleeve 40.

FIGS. 25 and 26 show that the optionally also screw thread-like tilting and/or bottom bevelled projections 99 for snap connection purposes and with corresponding counter projections 124, which can rest on the top of the casing 37 of the actuating unit 26, can be constructed as circumferentially mutually displaced segments, so that, like all the other parts of the dispenser described (except for the needle and possible compression springs) can be manufactured in easily demouldable manner from plastic injection moulded material. FIG. 27 shows the segments 99 and 124 in conjunction with the casing 37. The facing locking segments 99 can be introduced through the corresponding openings 100 into the recesses 101 and can be brought into the secured position by rotation. The counter segments 124 rest on the surface of the casing 37.

FIG. 28 shows a construction of a dispenser having a pretensioned, releasable actuating device 26. The cartridge-like dispenser unit 11 can correspond as regards construction and function to that of FIG. 22. It is inserted through the opening 114 into the casing 37 of the actuating unit 26 and is fixed by bayonet/screw/snap fastening. The screw cap is secured to the dispenser unit by means of a tear-up closure 117, 118 corresponding to FIG. 21 or 22.

In its substantially cylindrical casing 37 the actuating unit contains a compression spring 109, which is enclosed and guided in two in each case cup-shaped guide sleeves 125, 126. The sleeve 125 is part of a base 127, which downwardly terminates the actuating unit 26 and is fixed by locking on the casing jacket 37.

The spring unit 128 comprising the compression spring 109 and guide sleeves 125, 126 is held in the tensioned state by a release element 129, which is shown perspectively in FIG. 29 and whose function is illustrated in FIG. 30. The release element comprises a plastic part with an oval ring 130, which in the normal state has the shape designated "N" in FIG. 30. On the in each case most curved apices of the oval are provided support webs 131, which on the left-hand back in FIG. 29 project upwards and downwards and on the right-hand front only downwards. On this side is shaped a release button 39 projecting through a casing opening. On said side projects upwards a retaining web 132 stiffened by ribs and whose retaining face 133, as can be seen in FIG. 28, can engage on the flange 119 of the protective cap 66.

The function is as follows. The dispenser unit 11 is inserted in the actuating unit 26 following the removal of the latter from a storage container. In the latter it is fixed by insertion in an opening provided for this purpose using a plunger located there and this corresponds to the aforementioned IMIGRAN system. The pressure exerted by the plunger in the storage container acts on the face 134 of a push rod 135, which projects towards the dispenser unit from the cup-shaped guide sleeve 126 and projects through the opening of the ring 130. Whereas in the released state, the ring 130 is somewhat widened by the guide sleeve 126, the ring 130 snaps back into its oval shape N (FIG. 30) again if the guide sleeve 126 has traversed it downwards, because the plunger 135 has a much smaller cross-section than the opening of the ring 130. The resulting shoulder 136 is supported following the tensioning of the compression spring 109 on the underside of the ring 130, which is in turn axially non-displaceably guided between the guide sleeve 125 and the annular projection 95 of the casing. When the compression spring 109 is in the tensioned state, the ring 130 of the release element 129 is in the relaxed state. As this is the storage state of the operating unit, this represents an advantage, because as a result there are no problems with tension decrease through the flow of plastic under load.

Prior to actuating the dispenser it is firstly necessary to remove the protective cap 66. It is torn up and removed by means of the tear-up tongue 117, 118, so that the flange 119, which had hitherto substantially prevented or at least hindered by means of the retaining face 133 and retaining web 132 a movement of the release button 39 now frees the same.

If a pressure is now exerted on the release button 39, the oval ring is brought from its unloaded form (N in FIG. 30) into its actuated form B. FIG. 30 shows that the shoulder 136 blocked by the ring in position N, is freed in position B, so that now the spring unit 128 can relax and the plunger 125 performs the pump actuation of the dispenser. This construction has the further advantage that it operates solely with the inherent resilience of the release element and there is no need to respect close fits. In fact the opening in the ring can be much larger than the sleeve 126, so that there is no need to fear jamming. It has a blocking action solely because as a result of the injection moulding process it has a correspondingly oval construction. When in engagement on the flange 119 of the protective cap 66, the retaining web 132 prevents the complete deformation of the ring to a shape freeing the shoulder. This need not be a circular shape and can instead be a less pronounced oval.

In a particularly preferred embodiment according to FIG. 31 the construction and function corresponding to FIG. 28 have the additional, following advantages. The protective cap 66 not only, as in FIG. 28, by means of the retaining face 133 and retaining web 132, the release when the protective cap is fitted, but also through an extension of the active faces 133 and/or the corresponding projection at the upper end of the retaining web 132, the latter also engages in the bayonet/screw/snap locking means in such a way that when the locking has not completely taken place the locking element or elements 99 prevent an actuation in that they prevent the corresponding widening of the oval in the case of pressure on the release button 39.

There is also a securing of the protective cap 66 against undesired refitting, which would accidentally or deliberately simulate a dispenser unit which had already been used. As is particularly shown in FIGS. 32 and 33, this takes place in that the protective cap has a spreading or expanding edge sloping downwards in the manner of a hat brim.

FIG. 32 shows the state with the protective cap removed and prior to fitting on the dispenser unit or after removal has taken place. It can be seen that the expanding edge has expanded to a diameter preventing insertion in an upwardly channel-like, circumferential edge 139 on the dispenser unit 11. Insertion is only possible with a special fitting device, which is used in manufacture and compresses the expanding edge to such an extent that it can be inserted into the channel 140 bounded by the edge 139.

FIG. 34 shows that the thus secured dispenser unit, which is manufactured as a corresponding recharging unit in this form and can be inserted by the user in the actuating unit. The edge 139 has a corresponding cutout through which the retaining web 132 "senses" the expanding edge 137 and if it is present blocks release.

This construction is also appropriate as a manual system operable without spring pretension. In this case manual actuation would be blocked by the retaining web (cf. also FIG. 43). The feature of the non-refittable protective cap 66 is appropriate for all constructions.

FIG. 35 shows a construction corresponding to that of FIG. 28. However, there are two facing release buttons 39, both of which are secured against actuation with the protective cap 66 fitted by means of a retaining web 132. Also in the case of this construction the additional retaining action comes into effect when the bayonet or screw or snap locking means is not in the retained or locked position.

The geometry of the oval ring 130 is such that only the pressure on both release buttons simultaneously leads to an actuation of the dispenser. Thus, it prevents accidental actuation (optionally also provides a child-proof construction).

The construction and function of the dispenser unit 11 according to FIG. 36 correspond to FIG. 24, only in that in place of the locking pressure point function the preset breaking ring 54 is provided, which is connected to the reception sleeve 40 by means of the material bridges 55 (cf. FIGS. 6 and 18).

FIG. 37 shows a construction corresponding to FIG. 36, but in which the protective cap 66 has inner projections or pins 141, which pass through openings in the outlet connection 20 and engage in the movement mechanism of the thrust piston pump. In the present case the pins 141 engage over the flange 22 of the media container 12. Thus, in the case of accidental release it cannot be shoved upwards and the needle 85 cannot pierce the piston-like stopper 14, so as to prevent pump operation.

As can be gathered from FIG. 38, the protective cap has an oval cross-section and is sufficiently flexible that as a result of pressure at right angles to the pins 141 the cap assumes a round or optionally oval shape in the other direction, so that the pins can be drawn out of the corresponding openings in the outlet connection 20.

They not only free the operating mechanism, i.e. the thrust piston pump, but also make it possible to remove the protective cap.

As with the constructions having an oval release ring 130, in place of an oval a random other shape could be chosen, which cooperates with the shape of the part corresponding thereto in such a way that with a deformation the corresponding action occurs. Thus, e.g. here the protective cap could be circular, if the cross-section of the outlet connection was oval with the longer axis in the direction of the pins or optionally flattenings on the outlet connection could suffice in conjunction with a circular protective cap cross-section. The same applies for the release ring 130, which could also have a circular or some other shape, e.g. a rhombic or square shape, and could cooperate with a correspondingly constructed shoulder 136.

FIGS. 39 to 42 show a construction corresponding with respect to its operating mechanism to that according to FIG. 28. It correspondingly has a lateral release button 39, a deformable release ring 130 and a retaining web 132, which cooperates with a flange 119 of the protective cap 66.

The dispenser unit 11 shown in FIGS. 41 and 42 has a locking means for fixing to the actuating unit 26, which cooperates with the fastening of the protective cap 66. On the protective cap flange 119, e.g. on two opposite points are provided bow-like, downwardly projecting elements 143, which carry a wedge-shaped connecting part 144 on two relatively thin and optionally tear-off webs 143. The bow-shaped element in each case engages over one of the locking elements 99, which are here constructed as a flatter bayonet projection, but can also have a screw pitch. The inclined face 145 of the wedge 144 forms an insertion bevel, which is necessary for the insertion of the dispenser unit from above into the corresponding recess of the actuating unit 26. This takes place under corresponding elastic pivoting of a retaining or locking lever 146, which is provided on the release element 129 in place of one of the supporting webs 131 in FIG. 29. This ensures that the dispenser unit 11 can only be inserted when the protective cap 66 is still intact and fitted to the unit. If the protective cap is removed by corresponding turning and shearing of the webs 143 and an attempt is made to charge such a dispensing unit, then the cooperation of the flat bayonet projection 39 and the locking lever 146 does not permit the pressing back of the same and the insertion of the dispenser unit.

For the release of the dispenser unit 11 from the actuating unit 26 following use a release button 115 is provided (cf.

also FIG. 40), on which is shaped a fork 147 which is wedge-shaped at its two free ends and which is shown in FIG. 39a. As shown in FIG. 39, said fork 147 engages between the projection 95 of casing 37 and the locking lever 146 and presses the same outwards, so that the locking elements 99 are freed and the dispenser unit 11 can be removed. The projections 99 can correspond both to a bayonet and also simply to snap locking without turning into an operating position.

Following the release of the protective cap, which can only take place when the dispenser unit 11 has been inserted in the actuating unit 26, the bottom wedge-shaped member drops freely downwards. It is then no longer possible to fit said dispenser unit on an actuating unit.

FIG. 40 shows a construction with a tear-up tongue on the protective cap 66, but the arrangement of the actuating and release buttons 39 and 115 is the same as for FIG. 39.

FIG. 43 shows an actuating unit 26 with manual actuation by means of an actuating pusher 56, as shown in FIGS. 7 to 9. It projects a relatively long way and on it can be placed a lid 148, which contains a reserve holder 149 for two rechargeable replacement dispenser units 11. They can be jammed in or can also be inserted by means of the screw-bayonet connection with propeller blade-like locking elements 99. With the head of their protective caps 66 they engage in corresponding depressions in the actuating shoulder 44, so that even in the case of violent movements they remain in position.

Thus, this constitutes a different construction to the reserve holder for "replacement cartridges" or their functional parts already shown in FIGS. 2 and 8.

In the vicinity of the actuating shoulders a two-armed locking lever 150 is. shaped onto the casing 37 and as a result of whose manufacture it can pivot in the direction of the arrow 151, i.e. counterclockwise. However, it is prevented from doing so by the flange 119 of the protective cap 66, so that it rests with its lower barrier surface 152 on an inner projection 153 of the actuating pusher and prevents an actuation before the protective cap is removed. On removing the protective cap 66, the locking lever 150 pivots counterclockwise into a position releasing actuation.

What is claimed is:

1. A dispenser for flowable media, for applying media to a person, comprising:
    an exchangeable dispenser unit (11) operable for a limited number of application strokes, having
    an outlet opening (19) in form of a spray nozzle,
    at least one closing and opening element (15, 16) located between a media container (12) and the outlet opening (19) said opening element (16) being spaced inwardly from the outlet opening (19) and
    an outlet channel located between the media container (12) and the spray nozzle (19); and
    said dispenser further comprising
    an actuating unit (26) that is separable from the dispenser unit (11), and that is reusable,
    the actuating unit (26) having functional parts at least contributing to actuation of the dispenser unit (11); and
    wherein the dispenser unit (11) includes a wall apart from the media container that encloses the opening and closing elements to protect the medium within the dispenser from contamination.

2. The dispenser according to claim 1, wherein the media container (12) is at least partly located within the outlet piece (20) containing the spray nozzle (19).

3. A dispenser for flowable media, for applying media to a person, comprising:
    an exchangeable dispenser unit (11) operable for a limited number of application strokes, having
    an outlet opening (19) in form of a spray nozzle,
    at least one closing and opening element (15, 16) located between a media container (12) and the outlet opening (19) said opening element (16) being spaced inwardly from the outlet opening (19), and
    an outlet channel located between the media container (12) and the spray nozzle (19); and
    said dispenser further comprising
    an actuating unit (26) that is separable from the dispenser unit (11) and that is reusable,
    the actuating unit (26) having functional parts at least contributing to actuation of the dispenser unit (11); and
    wherein the dispenser unit (11) includes a wall apart from the media container that, encloses the opening and closing elements to protect the medium within the dispenser from contamination, and
    wherein the media container (12) also forms a pump cylinder of a thrust piston pump, and wherein a closing element of the media container (12) is formed by a piston-type stopper being pierceable by an opening element including a hollow needle (16), and wherein a push rod (18) receives the hollow needle, the push rod having an end face (24) pressing onto the piston-type stopper (14) to perform a pump stroke, the push rod (18) being located in the outlet piece (20) containing the spray nozzle (19).

4. The dispenser according to claim 3, wherein a narrow sealing gap (120) is provided between a casing part (95) of the dispenser unit (11) and a reception sleeve (40) receiving the media container.

5. The dispenser according to claim 3, wherein the actuating unit (26) has a charging chamber in which the dispenser unit (11) can be inserted.

6. The dispenser according to claim 3, wherein the actuating unit comprises a tensionable and releasable actuating mechanism.

7. A dispenser for flowable media, for applying media to a person, comprising:
    an exchangeable dispenser unit (11) operable for a limited number of application strokes, having
    an outlet opening (19) in form of a spray nozzle,
    at least one closing and opening element (15, 16) located between a media container (12) and the outlet opening (19), and
    an outlet channel located between the media container (12) and the spray nozzle (19); and
    said dispenser further comprising
    an actuating unit (26) that is separable from the dispenser unit (11) and that is reusable,
    the actuating unit (26) having functional parts at least contributing to actuation of the dispenser unit (11); and
    wherein the dispenser unit (11) encloses the opening and closing elements to protect the medium within the dispenser from contamination, and
    further comprising actuating pressure point means for ensuring a minimum actuating force for the dispenser.

8. The dispenser according to claim 7, wherein the actuating pressure point means are provided by destructible material bridges (55).

9. A dispenser for flowable media, for applying media to a person, comprising:
    an exchangeable dispenser unit (11) operable for a limited number of application strokes, having
    an outlet opening (19) in form of a spray nozzle,
    at least one closing and opening element (15, 16) located between a media container (12) and the outlet opening (19), and an outlet channel located between the media container (12) and the spray nozzle (19); and said dispenser further comprising an actuating unit (26) that is separable from the dispenser unit (11) and that is reusable, the actuating unit (26) having functional parts at least contributing to actuation of the dispenser unit (11); and wherein the dispenser unit (11) encloses the opening and closing elements to protect the medium within the dispenser from contamination, and wherein the actuating unit (26) is shaped like a round cylinder, having one end face providing a recess with fixing means for the dispenser unit (11).

10. A dispenser for flowable media, for applying media to a person, comprising:

an exchangeable dispenser unit (11) operable for a limited number of application strokes, having an outlet opening (19) in form of a spray nozzle, at least one closing and opening element (15, 16) located between a media container (12) and the outlet opening (19), and an outlet channel located between the media container (12) and the spray nozzle (19); and said dispenser further comprising an actuating unit (26) that is separable from the dispenser unit (11) and that is reusable, the actuating unit (26) having functional parts at least contributing to actuation of the dispenser unit (11); and wherein the dispenser unit (11) encloses the opening and closing elements to protect the medium within the dispenser from contamination, and wherein the actuating unit comprises a tensionable and releasable actuating mechanism, the actuating mechanism contains a release mechanism having a shape--variable ring (130), which has a release shape (B) closer to a circle shape than a blocking oval shape (N).

11. A dispenser for flowable media, for applying media to a person, comprising:

an exchangeable dispenser unit (11) operable for a limited number of application strokes, having an outlet opening (19) in form of a spray nozzle, at least one closing and opening element (15, 16) located between a media container (12) and the outlet opening (19), and an outlet channel located between the media container (12) and the spray nozzle (19); and said dispenser further comprising an actuating unit (26) that is separable from the dispenser unit (11) and that is reusable, the actuating unit (26) having functional parts at least contributing to actuation of the dispenser unit (11); and wherein the dispenser unit (11) encloses the opening and closing elements to protect the medium within the dispenser from contamination, and further comprising actuation blocking means for preventing undesired actuation of the dispenser (25).

12. The dispenser according to claim 11, wherein the blocking means cooperate with means (88, 89, 132, 133, 150) dependent on proper insertion of the dispenser unit (11) in the actuating unit (26).

13. The dispenser according to claim 11, wherein the blocking means contain a locking element (132, 150), which cooperates with the dispenser unit and with a release element (129).

14. The dispenser according to claim 11, wherein, for preventing actuation prior to the removal of a protective cap (66), the blocking means cooperate with a protective cap (66) for the dispenser unit (11).

15. A dispenser for flowable media, for applying media to a person, comprising:

an exchangeable dispenser unit (11) operable for a limited number of application strokes, having an outlet opening (19) in form of a spray nozzle, at least one closing and opening element (15, 16) located between a media container (12) and the outlet opening (19), and an outlet channel located between the media container (12) and the spray nozzle (19); and said dispenser further comprising an actuating unit (26) that is separable from the dispenser unit (11) and that is reusable, the actuating unit (26) having functional parts at least contributing to actuation of the dispenser unit (11); and wherein the dispenser unit (11) encloses the opening and closing elements to protect the medium within the dispenser from contamination, and further comprising a protective cap being prevented from being drawn off from the dispenser unit by locking means (85, 86) before the dispenser is ready to operate.

\* \* \* \* \*

UNITED STATES PATENT AND TRADEMARK OFFICE
CERTIFICATE OF CORRECTION

PATENT NO. : 6,708,846 B1
DATED : March 23, 2004
INVENTOR(S) : Karl-Heinz Fuchs

It is certified that error appears in the above-identified patent and that said Letters Patent is hereby corrected as shown below:

Column 10,
Line 30, "cat" should be -- can --.

Signed and Sealed this

Tenth Day of August, 2004

JON W. DUDAS
*Acting Director of the United States Patent and Trademark Office*